US009700049B2

(12) United States Patent
Funke et al.

(10) Patent No.: US 9,700,049 B2
(45) Date of Patent: Jul. 11, 2017

(54) ANTHRANILAMIDES IN COMBINATION WITH FUNGICIDES

(71) Applicant: BAYER INTELLECTUAL PROPERTY GMBH, Monheim am Rhein (DE)

(72) Inventors: Christian Funke, Leichlingen (DE); Heike Hungenberg, Langenfeld (DE); Ruediger Fischer, Pulheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/995,127

(22) Filed: Jan. 13, 2016

(65) Prior Publication Data

US 2016/0128331 A1    May 12, 2016

Related U.S. Application Data

(63) Continuation of application No. 13/177,752, filed on Jul. 7, 2011, now Pat. No. 9,265,255.

(60) Provisional application No. 61/361,991, filed on Jul. 7, 2010.

(30) Foreign Application Priority Data

Jul. 7, 2010    (EP) .................................. 10168700

(51) Int. Cl.
| | | |
|---|---|---|
| *A01N 43/713* | (2006.01) | |
| *A01N 43/56* | (2006.01) | |
| *A01N 25/00* | (2006.01) | |
| *A01N 43/54* | (2006.01) | |
| *A01N 43/707* | (2006.01) | |
| *A01N 43/88* | (2006.01) | |
| *A01N 57/12* | (2006.01) | |

(52) U.S. Cl.
CPC ........... *A01N 43/713* (2013.01); *A01N 25/00* (2013.01); *A01N 43/54* (2013.01); *A01N 43/56* (2013.01); *A01N 43/707* (2013.01); *A01N 43/88* (2013.01); *A01N 57/12* (2013.01)

(58) Field of Classification Search
CPC ........ A01N 43/88; A01N 43/54; A01N 57/12; A01N 43/707; A01N 43/713; A01N 43/56; A01N 25/00
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,789,566 A | 8/1998 | Bonhomme et al. | |
| 5,866,782 A | 2/1999 | Iwabuchi et al. | |
| 5,876,739 A | 3/1999 | Turnblad et al. | |
| 6,229,072 B1 | 5/2001 | Burns et al. | |
| 9,265,255 B2 * | 2/2016 | Funke | A01N 43/713 |
| 2003/0176428 A1 | 9/2003 | Schneidersmann et al. | |
| 2003/0229050 A1 | 12/2003 | Lahm et al. | |
| 2010/0029478 A1 | 2/2010 | Alig et al. | |
| 2010/0168042 A1 | 7/2010 | Funke et al. | |
| 2010/0256195 A1 | 10/2010 | Fischer et al. | |

FOREIGN PATENT DOCUMENTS

| | | | |
|---|---|---|---|
| DE | 10 2006 032 168 | 12/2007 | |
| DE | EP 2014166 A1 * | 1/2009 | ............. A01N 43/58 |
| DE | WO 2010025870 A1 * | 3/2010 | ............. A01N 43/82 |
| WO | 89/10396 | 11/1989 | |
| WO | 91/02069 | 2/1991 | |
| WO | 92/05251 | 4/1992 | |
| WO | 95/09910 | 4/1995 | |
| WO | 98/27806 | 7/1998 | |
| WO | 02/28186 | 4/2002 | |
| WO | 02/080675 | 10/2002 | |
| WO | 2004/046129 | 6/2004 | |
| WO | 2005/048712 | 6/2005 | |
| WO | 2006/021972 | 3/2006 | |
| WO | 2007144100 | 12/2007 | |
| WO | 2008/034785 | 3/2008 | |
| WO | 2010/069502 | 6/2010 | |

OTHER PUBLICATIONS

International Search Report Based on PCT/EP2011/061213 Mailed Mar. 20, 2012.
Baur et al.; "Polydisperse Ethoxylated Fatty Alcohol Surfactants as Accelerators of Cuticular Penetration. 1. Effects of Ethoxy Chain Length and the Size of the Penetrants"; Pestic. Sci.; 1997; vol. 51; pp. 131-152; SCI.
Colby; "Calculating Synergistic and Antagonistic Responses of Herbicide Combinations"; Weeds; 1967; vol. 15; pp. 20-22.

* cited by examiner

*Primary Examiner* — John Pak
*Assistant Examiner* — Andriae M Holt
(74) *Attorney, Agent, or Firm* — McBee Moore Woodward Vanik LLC; Susan McBee; David Woodward

(57) ABSTRACT

The present invention relates to novel active compound combinations which include of the insecticidally active compounds of the formula (I) in combination with fungicidally active compounds (II) and are highly suitable for controlling unwanted animal pests, such as insects, and unwanted phytopathogenic fungi.

14 Claims, No Drawings

ANTHRANILAMIDES IN COMBINATION WITH FUNGICIDES

CROSS REFERENCE TO RELATED APPLICATIONS

This application is a Continuation of pending U.S. application Ser. No. 13/177,752 filed Jul. 7, 2011, which claims priority to U.S. Provisional Application No. 61/361,991 filed Jul. 7, 2010, the contents of which are incorporated by reference in their entireties.

FIELD OF INVENTION

The present invention relates to novel active compound combinations which consist of the insecticidally active compounds of the formula (I) in combination with fungicidally active compounds (II) and are highly suitable for controlling unwanted animal pests, such as insects, acari and/or nematodes, and unwanted phytopathogenic fungi.

DESCRIPTION OF RELATED ART

Some of the anthranilamides of the formula (I) are already known from WO 2007/144100, and their insecticidal action has been described. The active compounds referred to in this description by their common name are known, for example, from "The Pesticide Manual" 14th Ed., British Crop Protection Council 2006, and the website http://www.alanwood.net/pesticides.

However, the insecticidal and/or fungicidal activity and/or the activity spectrum and/or the plant compatibility of the known compounds, especially with respect to crop plants, is not always adequate.

SUMMARY OF THE INVENTION

It has now been found that active compound combinations comprising the compounds of the general formula (I)

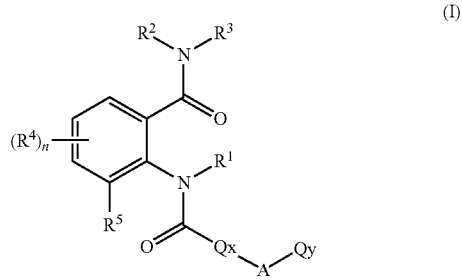

(I)

in which
R$^1$ represents hydrogen, amino, hydroxyl or represents C$_1$-C$_6$-alkyl, C$_2$-C$_6$-alkenyl, C$_2$-C$_6$-alkynyl or C$_3$-C$_6$-cycloalkyl, each of which is optionally mono- or polysubstituted by identical or different substituents, where the substituents independently another may be selected from the group consisting of halogen, cyano, nitro, hydroxyl, C$_1$-C$_4$-alkoxy, C$_1$-C$_4$-alkylthio, C$_1$-C$_4$-alkylsulphinyl, C$_1$-C$_4$-alkylsulphonyl, (C$_1$-C$_4$-alkoxy)carbonyl, C$_1$-C$_4$-alkylamino, di-(C$_1$-C$_4$-alkyl)amino, C$_3$-C$_6$-cycloalkylamino and (C$_1$-C$_4$-alkyl)-C$_3$-C$_6$-cycloalkylamino,
R$^2$ represents hydrogen, C$_1$-C$_6$-alkyl, C$_2$-C$_6$-alkenyl, C$_2$-C$_6$-alkynyl, C$_3$-C$_6$-cycloalkyl, C$_1$-C$_4$-alkoxy, C$_1$-C$_4$ alkylamino, di-(C$_1$-C$_4$-alkyl)amino, C$_3$-C$_6$-cycloalkylamino, C$_1$-C$_6$-alkoxycarbonyl or C$_1$-C$_6$-alkylcarbonyl,
R$^3$ represents hydrogen or represents C$_1$-C$_6$-alkyl, C$_1$-C$_6$-alkoxy, C$_2$-C$_6$-alkenyl, C$_2$-C$_6$-alkynyl, C$_3$-C$_{12}$-cycloalkyl, C$_3$-C$_{12}$-cycloalkyl-C$_1$-C$_6$-alkyl, each of which is optionally mono- or polysubstituted by identical or different substituents, where the substituents independently of one another may be selected from the group consisting of amino, C$_3$-C$_6$-cycloalkylamino, halogen, cyano, carboxyl, carbamoyl, nitro, hydroxyl, C$_1$-C$_6$-alkyl, C$_1$-C$_6$-haloalkyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_6$-alkoxycarbonyl, C$_1$-C$_6$-alkylcarbonyl, C$_3$-C$_6$-trialkylsilyl and a saturated or partially saturated heterocyclic ring, an aromatic or heteroaromatic ring or a saturated, partially saturated or aromatic heterobicyclic ring, where the ring or the ring system is optionally mono- or polysubstituted by identical or different substituents from the group consisting of SF$_5$, halogen, cyano, nitro, hydroxyl, amino, carboxyl, carbamoyl, aminosulphonyl, C$_1$-C$_6$-alkyl, C$_3$-C$_6$-cycloalkyl, C$_1$-C$_4$-alkoxy, C$_1$-C$_6$-haloalkyl, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-alkylsulphimino, C$_1$-C$_4$-alkylsulphimino-C$_1$-C$_4$-alkyl, C$_1$-C$_4$-alkylsulphimino-C$_2$-C$_5$-alkylcarbonyl, C$_1$-C$_4$-alkylsulphoximino, C$_1$-C$_4$-alkylsulphoximino-C$_1$-C$_4$-alkyl, C$_1$-C$_4$-alkylsulphoximino-C$_2$-C$_5$-alkylcarbonyl, C$_1$-C$_6$-alkoxycarbonyl, C$_1$-C$_6$-alkylcarbonyl, C$_3$-C$_6$-trialkylsilyl, benzyl C$_2$-C$_6$-alkenyl, C$_2$-C$_6$-alkynyl, C$_2$-C$_6$-haloalkenyl, C$_2$-C$_6$-haloalkynyl, C$_3$-C$_6$-halocycloalkyl, C$_1$-C$_4$-haloalkylthio, C$_1$-C$_4$-haloalkylsulphinyl, C$_1$-C$_4$-haloalkylsulphonyl, C$_1$-C$_4$-alkylamino, di-(C$_1$-C$_4$-alkyl)amino, C$_3$-C$_6$-cycloalkylamino and a 3- to 6-membered ring, where the ring may optionally be substituted by C$_1$-C$_6$-alkyl, halogen, cyano, nitro, halo-(C$_1$-C$_6$)-alkyl, C$_1$-C$_6$-alkoxy or halo-(C$_1$-C$_6$)-alkoxy, or
R$^3$ represents C$_1$-C$_6$-alkoxycarbonyl, C$_1$-C$_6$-alkylcarbonyl, C$_1$-C$_6$-alkylaminocarbonyl or di-(C$_1$-C$_6$)-alkylaminocarbonyl, or
R$^3$ furthermore represents a 5- or 6-membered aromatic or heteroaromatic ring, a 4-, 5- or 6-membered partially saturated ring or saturated heterocyclic ring, or a saturated, partially saturated or aromatic heterobicyclic ring which may optionally contain one to three heteroatoms from the group consisting of O, S and N, which rings are mono- or polysubstituted by identical or different substituents, where the substituents independently of one another are selected from the group consisting of SF$_5$, halogen, cyano, nitro, hydroxyl, amino, carboxyl, carbamoyl, C$_1$-C$_6$-alkyl, C$_3$-C$_6$-cycloalkyl, C$_1$-C$_4$-alkoxy, C$_1$-C$_6$-haloalkyl, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-alkylsulphimino, C$_1$-C$_4$-alkylsulphimino-C$_1$-C$_4$-alkyl, C$_1$-C$_4$-alkylsulphimino-C$_1$-C$_5$-alkylcarbonyl C$_1$-C$_4$-alkylsulphoximino, C$_1$-C$_4$-alkylsulphoximino-C$_1$-C$_4$-alkyl, C$_1$-C$_4$-alkylsulphoximino-C$_2$-C$_5$-alkylcarbonyl, C$_1$-C$_6$-alkoxycarbonyl, C$_1$-C$_6$-alkylcarbonyl, C$_2$-C$_6$-alkenyl, C$_2$-C$_6$-alkynyl, C$_2$-C$_6$-haloalkenyl, C$_2$-C$_6$-haloalkynyl, C$_3$-C$_6$-halocycloalkyl, C$_1$-C$_4$-haloalkylthio, C$_1$-C$_4$-haloalkylsulphinyl, C$_1$-C$_4$-haloalkylsulphonyl, C$_1$-C$_4$-alkylamino, di-(C$_1$-C$_4$-alkyl)amino and C$_3$-C$_6$-cycloalkylamino, or a 3- to 6-membered ring, where the ring may optionally be substituted by C$_1$-C$_6$-alkyl, halogen, cyano, nitro, halo-(C$_1$-C$_6$)-alkyl, C$_1$-C$_6$-alkoxy or halo-(C$_1$-C$_6$)-alkoxy, R² and R³ may be linked with each other via two to six carbon atoms and form a ring which optionally additionally contains a further nitrogen, sulphur or oxygen atom and which may optionally be mono- to tetrasubstituted by $C_1$-$C_2$-alkyl, $C_1$-$C_2$-haloalkyl, halogen, cyano, amino, $C_1$-$C_2$-alkoxy or $C_1$-$C_2$-haloalkoxy, R², R³ furthermore together represent $=S(C_1$-$C_4$-alkyl$)_2$ or $=S(O)(C_1$-$C_4$-alkyl$)_2$, R⁴ represents hydrogen, halogen, cyano, nitro $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two R⁴, via adjacent carbon atoms, form a ring which represents —$(CH_2)_3$—, —$(CH_2)_4$—, —$(CH_2)_5$—, —(CH=CH—)$_2$—, —$OCH_2O$—, —$O(CH_2)_2O$—, —$OCF_2O$—, —$(CF_2)_2O$—, —$O(CF_2)_2O$—, —(CH=CH—CH=N)— or —(CH=CH—N=CH)—, two R⁴ furthermore, via adjacent carbon atoms, form the fused rings below, which are optionally mono- or polysubstituted by identical or different substituents, where the substituents independently of one another may be selected from the group consisting of hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio-($C_1$-$C_6$-alkyl), $C_1$-$C_4$-alkysulphinyl-($C_1$-$C_6$-alkyl), $C_1$-$C_4$-alkylsulphonyl-($C_1$-$C_6$-alkyl), $C_1$-$C_4$-alkylamino, di-($C_1$-$C_4$-alkyl)amino and $C_3$-$C_6$-cycloalkylamino,

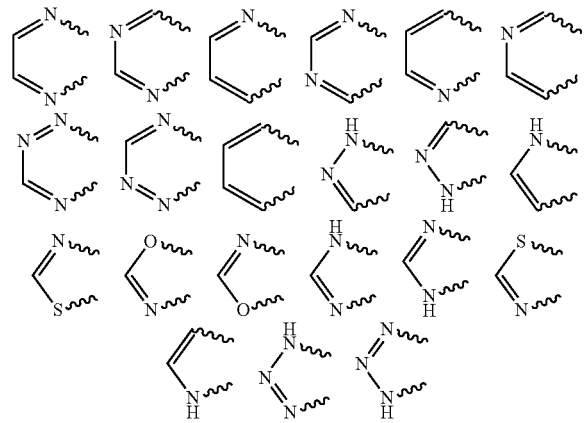

n represents 0 to 3,

R⁵ represents $C_1$-$C_6$-alkyl, $C_3$-$C_6$-cycloalkyl, $C_1$-$C_6$-haloalkyl, $C_1C_6$-halocycloalkyl, $C_2C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $Q_X$ represents an aromatic or heteroaromatic 5- or 6-membered ring which is optionally mono- or polysubstituted by identical or different R⁷ substituents and Which may contain 1-3 heteroatoms from the group consisting of N, S and O, A represents optionally mono- or polysubstituted —($C_1$-$C_6$-alkylene)-, —($C_2$-$C_6$-alkenylene)-, —($C_2$-$C_6$-alkynylene)-, —R⁸—($C_3$-$C_6$-cycloalkyl)-R⁸—, —R⁸—O—R⁸—, —R⁸—S—R⁸—, —R⁸—S(=O)—R⁸—, —R⁸—S(=O)$_2$—R⁸—, —R⁸—N($C_1$-$C_6$-alkyl)-R⁸—, —R⁸—C=NO($C_1$-$C_6$-alkyl)-R⁸, —CH[$CO_2$($C_1$-$C_6$-alkyl)]-, —R⁸—C(=O)—R⁸, —R⁸—C(=O)NH—R⁸, R⁸—C(=O)N($C_1$-$C_6$-alkyl)-R⁸, —R⁸—C(=O)NHNH—R⁸—, —R⁸—C(=O)N($C_1$-$C_6$-alkyl)-NH—R⁸—, —R⁸—C(=O)NHN($C_1$-$C_6$-alkyl)-R⁸, —R⁸—O(C=O)—R⁸, —R⁸—O(C=O)NH—R⁸, —R⁸—O(C=O)N($C_1$-$C_6$-alkyl)-R⁸, —R⁸—S(=O)$_2$NH—R⁸, —R⁸—S(=O)$_2$N($C_1$-$C_6$-alkyl)-R⁸, —R⁸—S(C=O)—R⁸, —R⁸—S(C=O)NH—R⁸, —R⁸—S(C=O)N($C_1$-$C_6$-alkyl)-R⁸, —R⁸—NHNH—R⁸, —R⁸—NHN($C_1$-$C_6$-alkyl)-R⁸, —R⁸—N($C_1$-$C_6$-alkyl)-NH—R⁸, —R⁸—N($C_1$-$C_6$-alkyl)-N($C_1$-$C_6$-alkyl)-R⁸, —R⁸—N=CH—O—R⁸, —R⁸—NH(C=O)O—R⁸, —R⁸—N($C_1$-$C_6$-alkyl)-(C=O)O—R⁸, —R⁸—NH(C=O)NH—R⁸, —R⁸—NH(C=S)NH—R⁸, —R⁸—NHS(=O)$_2$—R⁸, R⁸—NH—R⁸, R⁸—C(=O)—C(=O)—R⁸, R⁸—C(OH)—R⁸, R⁸—NH(C=O)—R⁸, R⁸-Qz-R⁸, R⁸—C(=N—NR'$_2$)—R⁸, R⁸—C(=C—R'$_2$)—R⁸ or —R⁸—N($C_1$-$C_6$-alkyl)S(=O)$_2$—R⁸, where the substituents independently of one another may be selected from the group consisting of halogen, cyano, nitro, hydroxyl, $C_1$-$C_6$-alkyl, $C_1$-$C_6$-alkyloxy, halo-$C_1$-$C_6$-alkyl, amino, ($C_1$-$C_6$-alkyl)amino, di-($C_1$-$C_6$-alkyl)amino and $C_3$-$C_6$-cycloalkyl where —($C_3$-$C_6$-cycloalkyl)- in the ring may optionally contain 1 or 2 heteroatoms selected from the group consisting of N, S and O, R⁸ represents straight-chain or branched —($C_1$-$C_6$-alkylene)- or represents a direct bond, where a plurality of R⁸ independently of one another represent straight-chain or branched —($C_1$-$C_6$-alkylene)- or represent a direct bond, for example, R⁸—O—R⁸— represents —($C_1$-$C_6$alkylene)-O—($C_1$-$C_6$-alkylene)-, —$C_1$-$C_6$-alkylene)-O—, —O—($C_1$-$C_6$-alkylene)-, or —O—, where R' represents alkyl, alkylcarbonyl, alkenyl, alkynyl, which may optionally be mono- or polysubstituted by halogen, $Q_Z$ represents a 3- or 4-membered partially saturated or saturated or a 5- or 6-membered partially saturated, saturated or aromatic ring or represents a 6- to 10-membered bicyclic ring system, where the ring or the bicyclic ring system may optionally contain 1-3 heteroatoms from the group consisting of N, S and O, where the ring or the bicyclic ring system is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl and di-($C_1$-$C_4$-alkyl)aminocarbonyl, $Q_Y$ represents a 5- or 6-membered partially saturated or saturated heterocyclic or heteroaromatic ring or an aromatic 8-, 9- or 10-membered fused heterobicyclic ring system, where the ring or the ring system is optionally mono- or polysubstituted by identical or different substituents and the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, nitro, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_6$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di-($C_1$-$C_4$-alkyl)aminocarbonyl, tri-($C_1$-$C_2$)alkylsilyl and ($C_1$-$C_4$-alkyl)($C_1$-$C_4$-alkoxy)imino, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, hydroxyl, $C_1$-$C_4$-alkoxy and $C_1$-$C_4$-haloalkoxy, $R^7$ represents hydrogen, $C_1$-$C_6$-alkyl, $C_2$-$C_6$-alkenyl, $C_2$-$C_6$-alkynyl, $C_3$-$C_6$-cy cloalkyl, $C_1$-$C_6$-haloalkyl, $C_2$-$C_6$-haloalkenyl, $C_3$-$C_6$-cycloalkoxy or

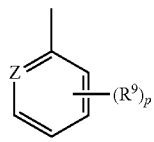

$R^9$ independently of one another represent hydrogen, $C_1$-$C_6$-alkyl, $C_3$-$C_6$-cycloalkyl, -$C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, p represents 0 to 4, Z represents N, CH, CF, CCl, CBr or Cl, the compounds of the general formula (I) further comprise N-oxides and salts, and one or snore fungicides from group (II):

Fungicides:

(1) Ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furcortazole-cis, hexaconazole, imazalil, imazalil sulphate, imibenconazole, ipconazole, metconazole, myclobutanil, naftifin, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, trialimefon, triadimenol, tridemorph, triflumizole, triforine, triticonazole, uniconazole, uniconazole-p, viniconazle, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H imidazole-1-carbothioate.

(2) Respiration inhibitors (respiratory chain inhibitors), such as, for example, bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoramethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide, 5,8-difluoro-N-[2-(2fluoro-4-{[4-(trifluoromethyl)pyridin-2-yl]oxy}phenyl)ethyl]quinazoline-4-amine, N-[9-(dichloromethylene)-1,2,3,4-tetrahydro-1,4-methanonaphthalen-5-yl]-3-(difluoromethyl)-1-methyl-1H-pyrazol-4-carboxamide, N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyramelostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethyliden}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl(2E)-2-{2-[({cyclopropyl[(4-methoxyphenyl)imino]methyl}sulphanyl)methyl]phenyl}-3-methoxyprop-2-enoate, N-(3-ethyl-3,5,5-trimethylcyclohexyl)-3-(formylamino)-2-hydroxybenzamide, 2-{2[(2,5-dimethylphenoxy)methyl]

phenyl}-2-methoxy-N-methylacetamide and (2R)-2-{2-[(2,5-dimethylphenoxy)methyl]phenyl}-2-methoxy-N-methylacetamide.
(4) Mitosis and cell division inhibitors, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.
(5) Compounds with multisite activity, for example Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations, for example calcium polysulphide, thiram, tolylfluanid, zineb and ziram.
(6) Resistance inductors, for example acibenzolar-S-methyl, isotianil, probenazole and tiadinil.
(7) Amino acid and protein biosynthesis inhibitors, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.
(8) ATP production inhibitors, for example fentin acetate, fentin chloride, fentin hydroxide and silthiofam.
(9) Cell wall synthesis inhibitors, for example benthiavalicarb, dimethomorph, flumorph, iprovalicarb, mandipropamid, polyoxins, polyoxorim, validamycin A and valifenalate.
(10) Lipid and membrane synthesis inhibitors, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.
(11) Melanin biosynthesis inhibitors, such as, for example, carpropamid, diclocymet, fenoxanil, phthalide, pyroquilon, tricyclazole and 2,2,2-trifluoroethyl{3-methyl-1-[(4-methylbenzoyl)amino]butan-2-yl}carbamate.
(12) Nucleic acid synthesis inhibitors, for example benalaxyl, benalaxyl-M (kiralaxyl), bupirimate, clozylacon, dimethirimol, ethirimol, furalaxyl, hymexazol, metalaxyl, metalaxyl-M(mefenoxam), ofurace, oxadixyl and oxolinic acid.
(13) Signal transduction inhibitors, for example chlozolinate, fenpiclonil, fludioxonil, iprodione, procymidone, quinoxyfen and vinclozolin.
(14) Decouplers, for example binaparyl, dinocap, ferimzone, fluazinam and meptyldinocap.
(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromide, flusulfamide, flutianil, fosetyl-aluminium, fosetyl-calcium, fosetyl-sodium, hexachlorobenzene, irumamycin, methasulfocarb, methyl isothiocyanate, metrafenon, mildiomycin, natamycin, nickel dimethyldithiocarbamate, nitrothal-isopropyl, octhilinone, oxamocarb, oxyfenthiin, pentachlorophenol and salts thereof, phenothrin, phosphoric acid and salts thereof, propamocarb-fosetylate, propanosine-sodium, proquinazid, pyrimorph, pyrrolnitrin, tebufloquin, tecloftalam, tolnifanid, triazoxide, trichlamide, zarilamide, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{-4-[(5R)-5-(2,6-difluorophenyl)-4,5-dihydro-1,2-oxazol-3-yl]-3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2yl}piperidin-1-yl)-2-[5-methyl-3-(triflouromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2,6-dimethyl-1-H,5H-[1,4]dithiino[2,3-c:5,6-c']dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts thereof, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulphonohydrazide, 5-fluoro-2-[(4-fluorobenzyl)oxy]pyrimidine-4-amine, 5-fluoro-2-[(4-methylbenzyl)oxy]pyrimidine-4-amine, 5-methyl-6-octyl[1,2,4]triazolo[1,5-a]pyrimidine-7-amine, ethyl(2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimideformamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulphate (2:1) and tert-butyl{6-[({[(1-methyl-1H-tetrazol-5-yl)(phenyl)methylene]amino}oxy)methyl]pyridin-2-yl}carbamate.

(16) further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl-]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide, 4-oxo-4-[(2-phenylethyl)amino]butanoic acid and but-3-yn-1-yl{6-[({[(Z)-(1-methyl-1H-tetrazol-5-yl)(phenyl)methylene]amino}oxy)methyl]pyridin-2-yl}carbamate are highly suitable for controlling unwanted animal pests such as insects, acari and/or nematodes and also unwanted phytopathogenic fungi.

If, within this description, the short form of the common name of an active compound is used, this in each case encompasses all common derivatives, such as the esters and salts, and isomers, especially optical isomers, especially the commercial form or forms. If an ester or salt is referred to by the common name, this also refers in each case to all other common derivatives, such as other esters and salts, the free acids and neutral compounds, and isomers, especially optical isomers, especially the commercial form or forms. The chemical compound names mentioned refer to at least one of the compounds encompassed by the common name, frequently a preferred compound.

Surprisingly, the insecticidal, acaricidal, nematicidal and fungicidal action of the active compound combinations according to the invention is considerably higher than the total of the actions of the individual active compounds. A true synergistic effect which could not have been predicted exists, not just a complementation of action.

DETAILED DESCRIPTION OF A PREFERRED EMBODIMENT

Preference is given to combinations comprising at least one of the active compounds of the formula (I) mentioned as being preferred, particularly preferred, very particularly preferred or especially preferred and one or more active compounds selected from group (II).

Preferred, particularly preferred, very particularly preferred or especially preferred are active compounds of the formula (I) where $R^1$ preferably represents hydrogen, $C_1$-$C_6$-alkyl, $C_2$-$C_6$-alkenyl, $C_2$-$C_6$-alkynyl, $C_3$-$C_6$-cycloalkyl, cyano-($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl, $R^1$ particularly preferably represents hydrogen, methyl, ethyl, cyclopropyl, cyanomethyl, methoxymethyl, methylthiomethyl, methylsulphinylmethyl or methylsulphonylmethyl, $R^1$ very particularly preferably represents hydrogen, $R^2$ preferably represents hydrogen or $C_1$-$C_6$-alkyl, $R^2$ particularly preferably represents hydrogen or methyl, $R^2$ very particularly preferably represents hydrogen, $R^3$ preferably represents hydrogen or represents $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, each of which is optionally mono- or polysubstituted by identical or different substituents, where the substituents independently of one another may be selected from the group consisting of halogen, cyano, carboxyl, carbamoyl, nitro, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkoxycarbonyl, $C_1$-$C_4$-alkylcarbonyl or a phenyl ring or a 4-, 5- or 6-membered aromatic, partially saturated or saturated heterocyclic ring, where the phenyl ring or heterocyclic ring is optionally mono- or polysubstituted by identical or different substituents and where the substituents independently of one another may be selected from the group consisting of hydrogen, $C_1$-$C_6$-alkyl, $C_2$-$C_6$-alkenyl, $C_2$-$C_6$-alkynyl, $C_3$-$C_6$-cycloakyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, carboxyl, carbamoyl, $NO_2$, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_6$-alkyl)carbonyl, ($C_1$-$C_6$-alkoxy)carbonyl or $R^3$ preferably represents $C_2$-$C_4$-alkoxycarbonyl, $C_2$-$C_4$-alkylcarbonyl, $C_2$-$C_4$-alkylaminocarbonyl or $C_2$-$C_4$-dialkylaminocarbonyl, or $R^3$ represents a phenyl ring, a 5- or 6-membered aromatic heterocyclic ring or a 4-, 5- or 6-membered partially saturated or saturated heterocyclic ring which may contain 1-3 heteroatoms from the group consisting of N, S and O, where the phenyl ring or heterocyclic ring is optionally mono- or polysubstituted by identical or different substituents, and where the substituents independently of one another may be selected from the group consisting of hydrogen, $C_1$-$C_4$-alkyl, $C_2$-$C_4$-alkenyl, $C_2$-$C_4$-alkynyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, carboxyl, carbamoyl, $NO_2$, hydroxyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di-($C_1$-$C_4$-alkyl)amino, $C_3$-$C_6$-cycloalkylamino, ($C_1$-$C_4$-alkyl)carbonyl and ($C_1$-$C_4$-alkoxy)carbonyl, $R^3$ particularly preferably represents hydrogen or represents $C_1$-$C_4$-alkyl or $C_3$-$C_6$-cycloalkyl, each of which is optionally mono- or polysubstituted by identical or different substituents, where the substituents independently of one another may be selected from the group consisting of halogen, cyano, carboxyl, hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_2$-$C_4$-alkoxycarbonyl, $C_2$-$C_6$-alkylcarbonyl and a phenyl ring and a 4-, 5- or 6-membered aromatic, partially saturated or saturated heterocyclic ring, where the phenyl ring or heterocyclic ring is optionally mono- or polysubstituted by identical or different substituents, and where the substituents independently of one another may be selected from the group consisting of hydrogen, $C_1$-$C_4$-alkyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, hydroxyl, $C_1$-$C_4$-alkoxy and $C_1$-$C_4$-haloalkoxy, or $R^3$ particularly preferably represents $C_2$-$C_4$-alkoxycarbonyl, $C_2$-$C_4$-alkylcarbonyl or $C_2$-$C_4$-alkylaminocarbonyl, or $R^3$ particularly preferably represents a phenyl ring, a 5- or 6-membered aromatic heterocyclic ring or a 4-, 5- or 6-membered partially saturated or saturated heterocyclic ring which may contain 1-3 heteroatoms from the group consisting of N, S and O, where the phenyl ring or heterocyclic ring is optionally mono- or polysubstituted by identical or different substituents, and where the substituents indepedently of one another may be selected from the group consisting of hydrogen, $C_1$-$C_4$-alkyl, $C_2$-$C_4$-alkenyl, $C_2$-$C_4$-alkenyl, $C_3$-$C_6$-cycloalkyl, $C_1$-$C_4$-haloalkyl, $C_2$-$C_4$-haloalkenyl, $C_2$-$C_4$-haloalkynyl, $C_3$-$C_6$-halocycloalkyl, halogen, cyano, carbamoyl, $NO_2$, hydroxyl, $C_1$-$C_4$-alkoxy and $C_1$-$C_4$-haloalkoxy, or $R^3$ very particularly preferably represents hydrogen, methyl, ethyl, n-propyl, isopropyl, n-butyl, isobutyl, sec-butyl, text-butyl, cyclopropyl, cyclobutyl, azetidine, oxetane, thietane, pyrrolidine, pyrazolidine, imidazolidine, imidazolidinone, tetrahydrofuran, tetrahydrothiophene, tetrahydrothiophene dioxide, thiazoline, thiazolidine, piperidine, piperazine, tetrahydropyran, dihydrofuranone, dioxane, morpholine, thiomorpholine, thiomorpholine dioxide, phenyl or pyridyl, or $R^3$ especially preferably represents hydrogen, methyl, isopropyl, cyclopropyl or tert-butyl.

$R^4$ preferably represents hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio, two adjacent radicals $R^4$ likewise preferably represent —$(CH_2)_3$—, —$(CH_2)_4$—, —$(CH_2)_5$—, —(CH=CH—)$_2$—, —$OCH_2O$—, —$O(CH_2)_2O$—, —$OCF_2O$—, —$(CF_2)_2O$—, —$O(CF_2)_2O$—, —(CH=CH—CH=N)— or —(CH=CH—N=CH)—, $R^4$ particularly preferably represents hydrogen, $C_1$-$C_4$-alkyl, $C_1$-$C_2$-haloalkyl, halogen, cyano or $C_1$-$C_2$-haloaikoxy, two adjacent radicals $R^4$ particularly preferably represent —$(CH_2)_4$—, —(CH=CH—)$_2$—, —$O(CH_2)_2O$—, —$O(CF_2)_2O$—, —(CH=CH—CH=N)— or —(CH=CH—N=CH)—, $R^4$ very particularly preferably represents hydrogen, methyl, trifluoromethyl, cyano, fluorine, chlorine, bromine, iodine or trifluoromethoxy. Moreover, two adjacent radicals $R^4$ very particularly preferably represent —$(CH_2)_4$— or —(CH=CH—)$_2$—, $R^4$ especially preferably represents chlorine, fluorine or bromine, $R^4$ furthermore especially preferably represents iodine or cyano, two adjacent radicals $R^4$ especially preferably represent —(CH=CH—)$_2$ n preferably represents 0, 1 or 2, n particularly preferably represents 1 or 2, n very particularly preferably represents 1, $R^5$ preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^5$ particularly preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl, $R^5$ very particularly preferably represents methyl, fluorine, chlorine, bromine or iodine, $R^5$ especially referably represents methyl or chlorine, $Q_X$ preferably represents a 5- or 6-membered heteroaromatic ring which is optionally mono- or polysubstituted by identical or different $R^7$ and which may contain 1-3 heteroatoms from the group consisting of N, O and S, or represents phenyl, $Q_X$ particularly preferably represents a 5- or 6-membered ring selected from the group consisting of furan, thiophene, triazole, imidazole, thiazole, oxazole, isoxazole, isothiazole, thiadiazole, oxadiazole, pyrrole, pyridine, pyrimidine, pyridazine, pyrazine, phenyl or pyrazole, which ring is optionally mono- or polysubstituted by identical or different $R^7$, $Q_X$ very particularly preferably represents thiazole, oxazole, pyrrole, imidazole, triazole, pyrimidine, phenyl or represents pyrazole which is monosubstituted by the group $R^7$,

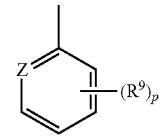

where Z, R and p may have the general definitions given above or the preferred or particularly preferred definitions given below, A preferably represents optionally mono- or polysubstituted —($C_1$-$C_4$-alkylene)-, —$C_2$-$C_4$-alkenylene)-, —($C_2$-$C_4$-alkynylene)-, —$R^8$—($C_3$-$C_6$-cycloalkyl)-$R^8$—, —$R^8$—O—$R^8$—, —$R^8$—S—$R^8$—, —$R^8$—S(=O)—$R^8$—, —$R^8$—S(=O)$_2$—$R^8$—, —$R^8$—NH—($C_1$-$C_4$-alkyl)-, —$R^8$—N($C_1$-$C_4$-alkyl)-$R^8$, —$R^8$—C=NO($C_1$-$C_4$-alkyl), —R⁸—C(=O)—R⁸, —R⁸—C(=S)—R⁸, —R⁸—C(=O)NH—R⁸, R⁸—C(=O)N(C₁-C₄-alkyl)-R⁸, —R⁸—S(=O)₂NH—R⁸, —R⁸—S(=O)₂N(C₁-C₄-alkyl)-R⁸, —R⁸—NH(C=O)O—R⁸, —R⁸—N(C₁-C₄-alkyl)-(C=O)O—R⁸, —R⁸—NH(C=O)NH—R⁸, —R⁸—NHS(=O)₂—R⁸, —R⁸—N(C₁-C₄-alkyl)S(=O)₂—R⁸, R⁸—NH—R⁸, R⁸—C(=O)—C(=O)—R⁸, R⁸—C(OH)—R⁸ or R⁸-Qz-R⁸, where the substituents independently of one another may be selected from the group consisting of halogen, cyano, nitro, hydroxyl, C₁-C₆-alkyl, C₁-C₆-alkoxy and halo-C₁-C₆-alkyl, where Q$_Z$ may have the general definitions given above or the preferred or particularly preferred definitions given below, A particularly preferably represents —CH₂—, —CH₂O—, —CH₂OCH₂—, —CH₂S—, —CH₂SCH₂—, —CH₂N(C₁-C₄-alkyl)-, —CH₂N(C₁-C₄-alkyl)CH₂—, —CH(Hal)-, —C(Hal)₂-, —CH(CN)—, CH₂(CO)—, CH₂(CS)—, CH₂CH(OH)—, -cyclopropyl-, CH₂(CO)CH₂—, —CH(C₁-C₄alkyl)-, —C(di-C₁-C₆-alkyl)-, —CH₂CH₂—, —CH=CH—, —C≡C—, —C=NO(C₁-C₆-alkyl) or —C(=O)(C₁-C₄-alkyl)-, A very particularly preferably represents —CH₂—, —CH(CH₃), C(CH₃)₂, —CH₂CH²—, —CH(CN)—, —CH₂O— or —C(=O)—CH₂—, A especially preferably represents CH₂, CH(CH₃), —CH₂O— or —C(=O)—CH₂—, Q$_Z$ preferably represents a 3- or 4-membered partially saturated or saturated or a 5- or 6-membered partially saturated, saturated or aromatic ring, where the ring may optionally contain 1-3 heteroatoms from the group consisting of N, S and O, where the ring is optionally mono- or polysubstituted by identical or different substituents, and where the substituents independently of one another may be selected from the group consisting of hydrogen, C₁-C₆-alkyl, C₂-C₆-alkenyl, C₂-C₆-alkynl, C₁-C₆-cycloalkyl, C₁-C₆-haloalkyl, C₂-C₆-haloalkenyl, C₂-C₆-haloalkynyl, C₃-C₆-halocycloalkyl, halogen, cyano, hydroxyl, C₁-C₄-alkoxy, C₁-C₄-haloalkoxy, C₁-C₄-alkylthio, C₁-C₄-alkylsulphinyl, C₁-C₄-alkylsulphonyl, C₁-C₄-haloalkylthio, C₁-C₄-haloalkysulphinyl and C₁-C₄-haloalkylsulphonyl, Q$_Z$ particularly preferably represents a 3- or 4-membered partially saturated or saturated or a 5-membered partially saturated, saturated or aromatic ring, where the ring may optionally contain 1-2 heteroatoms from the group consisting of N, S and O, where the ring is optionally mono- or polysubstituted by identical or fferent substituents, and where the substituents independently of one another may be selected from the group consisting of hydrogen, C₁-C₆-alkyl, C₂-C₆-alkenyl, C₂-C₆-alkynyl, C₃-C₆-cycloalkyl, C₁-C₆-haloalkyl, C₂-C₆-haloalkenyl, C₂-C₆-haloalkynyl, C₃-C₆-halocycloalkyl, halogen, cyano, hydroxyl, C₁-C₄-alkoxy, C₁-C₄-haloalkoxy, C₁-C₄-alkylthio, C₁-C₄-alkylsulphinyl, C₁-C₄-alkylsulphonyl, C₁-C₄-haloalkylthio, C₁-C₄-haloalkylsulphinyl and C₁-C₄-haloalkylsulphonyl, Q$_Z$ very particularly preferably represents azetidine, oxetane or thietane, pyrrolidine, pyrroline, pyrazolidine, pyrazoline, imidazolidine, imidazolidone, imidazoline, tetrahydrofuran, tetrahydrothiophene, thiazolidine, isothiazolidine or isoxazoline, which is optionally mono- or polysubstituted by identical or different substituents, and where the substituents independently of one another may be selected from the group consisting of hydrogen, methyl, ethyl, isopropyl, hydroxyl, methoxy, trifluoromethoxy, fluorine, chlorine, bromine, cyano, difluoromethyl, trifluoromethyl, R⁷ preferably represents C₁-C₆-alkyl or represents the radical

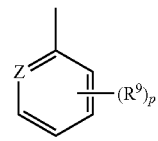

R⁷ furthermore preferably represents C₃-C₆-cycloalkoxy,

R⁷ particularly preferably represents methyl or represents the radical

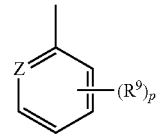

R⁹ independently of one another preferably represent hydrogen, halogen, cyano, C₁-C₆-alkyl, C₁-C₄-alkoxy, C₁-C₄-haloalkyl, C₁-C₄-haloalkoxy, C₁-C₄-haloalkylsulphonyl or (C₁-C₄-alkyl)-C₁-C₄-alkoxyimino, R⁹ independently of one another particularly preferably represent hydrogen, halogen, cyano or C₁-C₄-haloalkyl, R⁹ independently of one another very particularly preferably represent fluorine, chlorine or bromine, R⁹ especially preferably represents chlorine, p preferably represents 1, 2 or 3, p particularly preferably represents 1 or 2, p very particularly preferably represents 1, Z Preferably represents N, CH, CF, CCl, CBr or CI, Z particularly preferably represents N, CH, CF, CCl or CBr, Z very particularly preferably represents N, CCl or CH, R⁸ preferably represents straight-chain or branched —(C₁-C₄-alkylene)- or represents a direct bond, R⁸ particularly preferably represents methyl, ethyl, propyl, isopropyl, n-butyl, sec-butyl or isobutyl or a direct bond, R⁸ very particularly preferably represents methyl or ethyl or a direct bond, Q$_Y$ Preferably represents a 5- or 6-membered partially saturated or saturated heterocyclic or heteroaromatic ring or an aromatic 8-, 9- or 10-membered fused heterobicyclic ring system, where the heteroatoms may be selected from the group consisting of N, S and O, where the ring or the ring system is optionally mono- or polysubstituted by identical or different substituents, and where the substituents independently of one another may be selected from the group consisting of hydrogen, C₁-C₆-alkyl, C₂-C₆-alkenyl, C₂-C₆-alkynyl, C₃-C₆-cycloalkyl, C₁-C₆-haloalkyl, C₂-C₆-haloalkenyl, C₂-C₆-haloalkynyl, C₃-C₆-halocycloalkyl, halogen, cyano, carboxyl, carbamoyl, nitro, hydroxyl, C₁-C₄-alkoxy, C₁-C₄-haloalkoxy, C₁-C₄-alkylthio, C₁-C₄-alkylsulphinyl, C₁-C₄-alkylsulphonyl, C₁-C₄-haloalkylthio, C₁-C₄-haloalkysulphinyl, C₁-C₄-haloalkylsulphonyl, or where the substituents independently of one another may be selected from the group consisting of phenyl and a 5- or 6-membered heteroaromatic ring, where phenyl or the ring may optionally be mono- or polysubstituted by identical or different substituents from the group consisting of C₁-C₆-alkyl, C₂-C₆-alkenyl, C₂-C₆-alkynyl, C₃-C₆- cycloalkyl, $C_1$-$C_6$-haloalkyl, $C_2$-$C_6$-haloalkenyl, $C_2$-$C_6$-haloalkynyl, $C_3$-$C_6$-halocyeloalkyl, halogen, cyano, nitro, hydroxyl, $C_2$-$C_4$-alkoxy and $C_1$-$C_4$-haloalkoxy, $Q_Y$ particularly preferably represents an optionally mono- or polysubstituted 5- or 6-membered heteroaromatic ring from the group consisting of Q-1 to Q-53 and Q-58 to Q-59, Q62 to Q63, an aromatic 9-membered fused heterobicyclic ring system Q-54 to Q-56 or a 5-membered heterocyclic ring Q-60 to Q-61, where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$alkynyl, $C_3$-$C_6$-cycloalkyl, $C_1$-$C_6$-haloalkyl, C-$C_6$-haloalkenyl, $C_2$-$C_6$-haloalkynyl, $C_3$-$C_6$-halocycloalkyl, halogen, cyano, $NO_2$, hydroxyl, $C_1$-$C_4$-alkoxy and $C_1$-$C_4$-haloalkoxy, $Q_Y$ very particularly preferably represents an optionally mono- or polysubstituted 5- or 6-membered heteroaromatic ring from the group consisting of Q-36 to Q-40, Q43, Q-58 to Q-59, Q62, Q63, an aromatic 9-membered fused heterobicyclic ring system Q-54 to Q-56 or a 5-membered heterocyclic ring Q-60 to Q-61, where the substituents independently of one another may be selected from the group consisting of $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or where the substituents independently of one another may be selected from the group consisting of phenyl and a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, cyano, nitro, $C_1$-$C_4$-alkoxy and $C_1$-$C_4$-haloalkoxy, $Q_Y$ especially preferably represents a heteroaromatic ring from the group consisting of Q-37, Q-38, Q-39, Q-40, Q43, Q-58, Q-59, Q62 and Q63 which is optionally mono- or polysubstituted by identical or different substituents, or represents a 5-membered heterocyclic ring Q-60, where the substituents independently of one another may be selected from the group consisting of methyl, ethyl, cyclopropyl, tert-butyl, chlorine, fluorine, iodine, bromo, cyano, nitro, difluoromethyl, trifluoromethyl, pentafluoroethyl, n-heptafluoropropyl and isoheptafluoropropyl or where the substituents independently of one another may be selected from the group consisting of phenyl and a 5- or 6-membered heteroaromatic ring, where the substituents independently of one another may be selected from the group consisting of methyl, ethyl, cyclopropyl, tert-butyl, chlorine, fluorine, iodine, bromine, cyano, nitro, difluoromethyl, trifluoromethyl, pentafluorethyl, n-heptafluoropropyl and isoheptafluoropropyl.

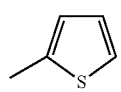

Q-1

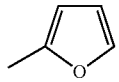

Q-2

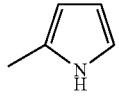

Q-3

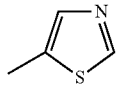

Q-4

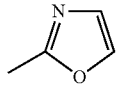

Q-5

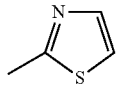

Q-6

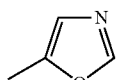

Q-7

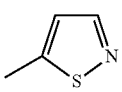

Q-8

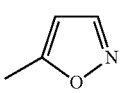

Q-9

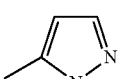

Q-10

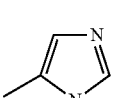

Q-11

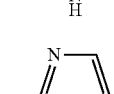

Q-12

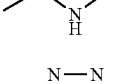

Q-13

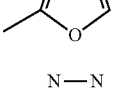

Q-14

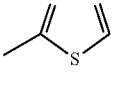

Q-15

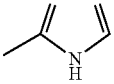

Q-16

-continued
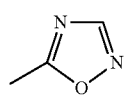 Q-17
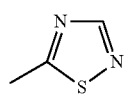 Q-18
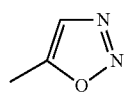 Q-19
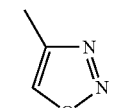 Q-20
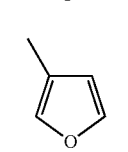 Q-21
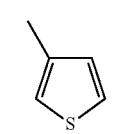 Q-22
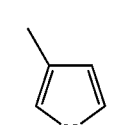 Q-23
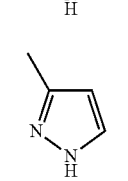 Q-24
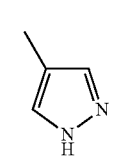 Q-25
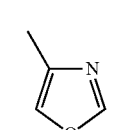 Q-26
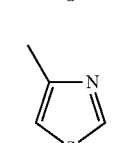 Q-27
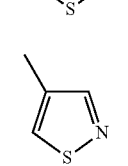 Q-28
-continued
 Q-29
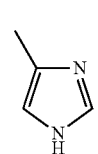 Q-30
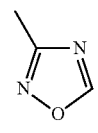 Q-31
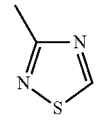 Q-32
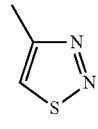 Q-33
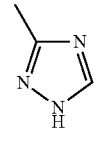 Q-34
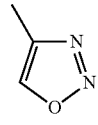 Q-35
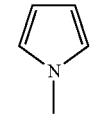 Q-36
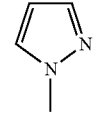 Q-37
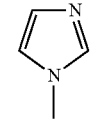 Q-38
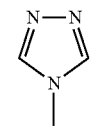 Q-39
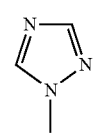 Q-40

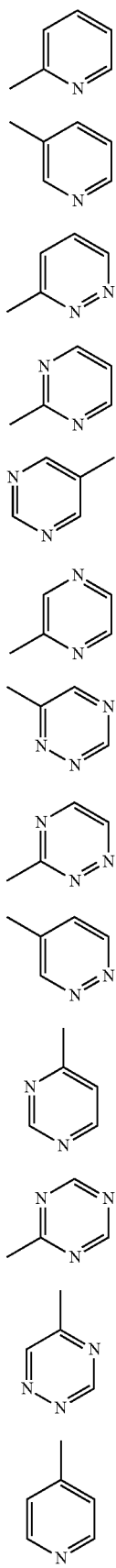
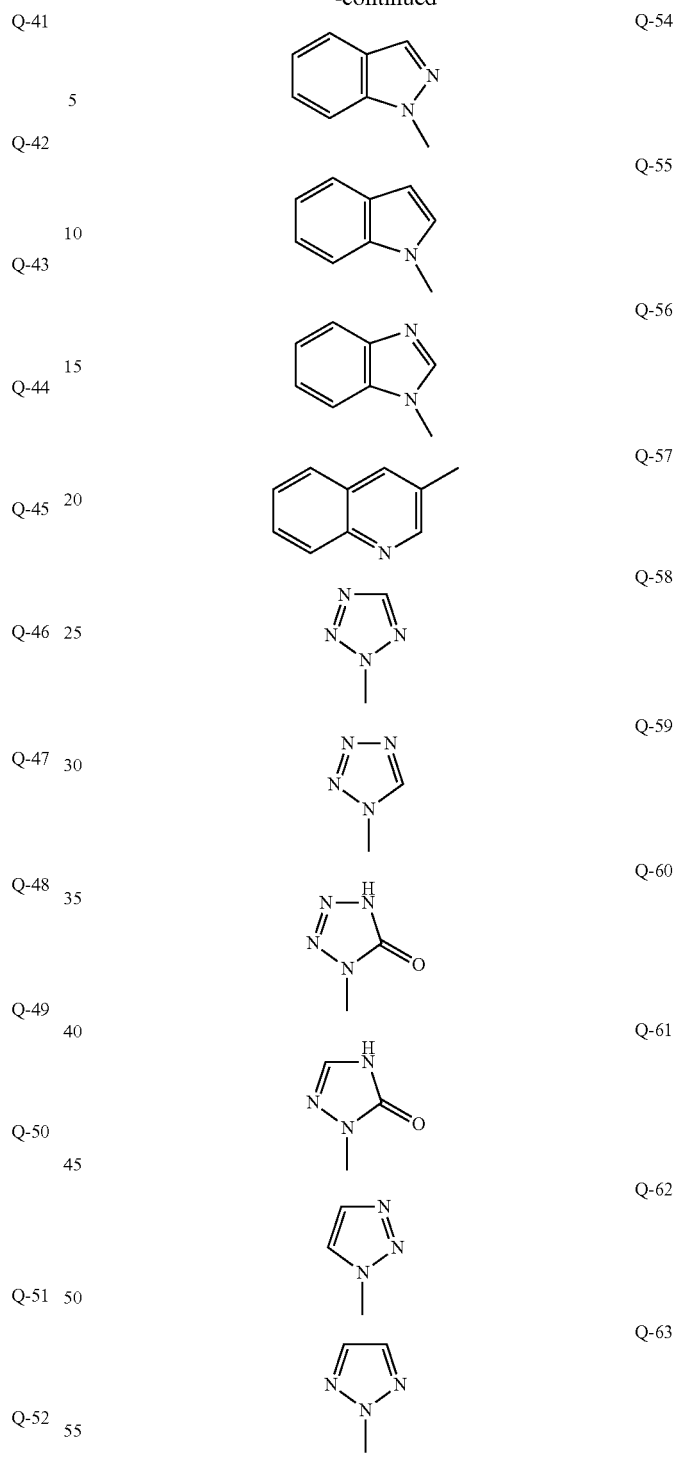

Independently of one another, the rings or ring systems listed above may additionally be substituted by oxo, thioxo, (=O)=NH, (=O)=N—CN, (=O)$_2$. Tetrahydrothiophene dioxide and imidazolidone may be mentioned by way of example.

In this case, the oxo group as substituent at a ring carbon atom, for example, is a carbonyl group in the heterocyclic ring. As a result, lactones and lactams are preferably also included. The oxo group may also be present at the hetero ring atoms which can occur in various oxidation states, for example at N and S, in which case they form, for example, the divalent groups —N(O)—, —S(O)— (also abbreviated as SO) and —S(O)$_2$— (also abbreviated as SO$_2$) in the heterocyclic ring. In the case of —N(O)— and —S(O)— groups, in each case both enantiomers are included.

At a heterocyclic ring, substituents other than the oxo group may also be attached to a heteroatom, for example at a nitrogen atom, if during the process a hydrogen atom at the nitrogen atom of the parent structure is replaced. In the case of the nitrogen atom and also other heteroatoms such as, for example, the sulphur atom, further substitution with formation of quaternary ammonium compounds or sulphonium compounds is also possible.

In particular, the compounds of the formula (I) can be present in the form of various regioisomers. For example in the form of mixtures of compounds having, the definition Q62 or Q63 or in the form of mixtures of Q58 and Q59. Accordingly, the invention also embraces active compound combinations comprising mixtures of compounds of the formula (I) where $Q_Y$ has the meanings Q62 and Q63, and also Q58 and Q59, and the compounds may be present in various mixing ratios, and one or more active compounds from group (II). Preference is given here to mixing ratios of compounds of the formula (I) in which the radical $Q_Y$ represents Q62 or Q58 to compounds of the formula (I) in which the radical Qy represents Q63 or Q59 of from 60:40 to 99:1, particularly preferably from 70:30 to 97:3, very particularly preferably from 80:20 to 95:5. Special preference is given to the following mixing ratios of a compound of the formula (I) where $Q_Y$ has the meaning Q62 or Q58 to a compound of the formula (I) where $Q_Y$ has the meaning Q63 or Q59: 80:20; 81:19; 82:18; 83:17; 84:16; 85:15; 86:14; 87:13; 88:12; 89:11; 90:10, 91:9; 92:8; 93:7; 96:6; 95:5.

Preference is furthermore given to active compound combinations comprising a east one active compound of the formula (I-1)

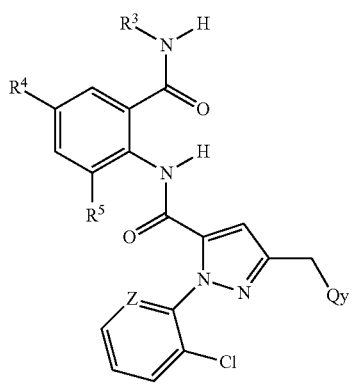

(I-1)

in which
R$^3$ represents hydrogen or represents C$_1$-C$_6$-alkyl, C$_1$-C$_6$-alkoxy, C$_2$-C$_6$-alkenyl, C$_2$-C$_6$-alkynyl, C$_3$-C$_{12}$-cycloalkyl, C$_3$-C$_{12}$-cycloalkyl-C$_1$-C$_6$-alkyl, each of which is optionally mono- or polysubstituted by identical or different substituents, where the substituents independently of one another may be selected from the group consisting of halogen, amino, cyano, nitro, hydroxyl, C$_1$-C$_6$-alkyl, C$_3$-C$_6$-cycloalkyl, C$_1$-C$_4$-alkoxy, C$_1$-C$_4$-haloalkoxy, C$_1$-C$_4$-alkylthio, C$_2$-C$_6$-alkoxycarbonyl, C$_1$-C$_6$-alkylcarbonyl, C$_3$-C$_6$-cycloalkylamino and a 5- or 6-membered heteroaromatic ring, R$^4$ represents halogen, cyano or methyl,
R$^5$ represents methyl or chlorine,
Z represents N, CCl or CH,
Qy represents an optionally mono- or polysubstituted 5- or 6-membered heteroaromatic ring from the group consisting of Q-36 to Q-40, Q43, Q-58 to Q-59, Q62, Q63, an aromatic 9-membered fused heterobicyclic ring system Q-54 to Q-56 or a 5-membered heterocyclic ring Q-60 to Q-61, where the substituents independently of one another may be selected from the group consisting of C$_1$-C$_3$-alkyl, C$_1$-C$_3$-haloalkyl, C$_1$-C$_2$-alkoxy, halogen, cyano, hydroxyl, nitro or C$_1$-C$_2$-haloalkoxy,
where the compounds of the formula (I-1) may be present in the form of salts,
and one or more active compounds selected from group (II).

Particular preference is given to combinations comprising at least one of the active compounds of the formula (I-1) mentioned as being preferred, particularly preferred, very particularly preferred or especially preferred and one or more active compounds selected from group (II).

Preferred, particularly preferred, very particularly preferred or especially preferred are active compounds of the formula (I-1) where
R$^3$ preferably represents hydrogen or represents C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, C$_3$-C$_6$-cycloalkyl-C$_1$-C$_6$alkyl, each of which is optionally mono- or polysubstituted by identical or different substituents, where the substituents independently of one another may be selected from the group consisting of halogen, cyano, amino, hydroxyl, C$_1$-C$_6$-alkyl, C$_1$-C$_4$-alkoxy, C$_1$-C$_4$-haloalkoxy, C$_1$-C$_4$-alkylthio, C$_3$-C$_6$-cycloalkyl and a 5- or 6-membered heteroaromatic ring which contains 1-2 heteroatoms from the group consisting of N, O and S, where two oxygen atoms in the ring are not adjacent,
R$^3$ particularly preferably represents one of the radicals below

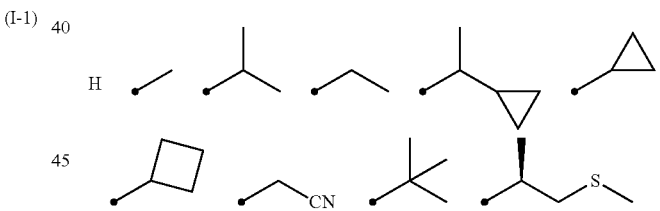

R$^4$ preferably represents halogen, cyano or methyl,
R$^4$ particularly preferably represents chlorine or cyano,
R$^4$ also particularly preferably represents bromine, fluorine, iodine or methyl,
R$^5$ preferably and particularly preferably represents methyl,
Z preferably represents N or CH,
$Q_Y$ preferably represents a heteroaromatic ring from the group consisting of Q-37, Q-38, Q-39, Q-40, Q43, Q-58, Q-59, Q62 and Q63 which is optionally mono- or polysubstituted by identical or different substituents, or represents a 5-membered heterocyclic ring Q-60, where the substituents independently of one another may be selected from the group consisting of methyl, ethyl, cyclopropyl, tert-butyl, chlorine, fluorine, iodine, bromo, cyano, nitro, difluoromethyl, trifluoromethyl, pentafluoroethyl, n-heptafluoropropyl and isoheptafluoropropyl,
$Q_Y$ particularly preferably represents a heteroaromatic ring from the group consisting of Q-58 and Q-59 which is optionally mono- or polysubstituted by identical or different substituents, where the substituents independently of one another may be selected from the group consisting of methyl, ethyl, cyclopropyl, tert-butyl, difluoromethyl, trifluoromethyl, pentafluoroethyl, n-heptafluoropropyl and isoheptafluoropropyl.

In particular, the compounds of the formula (I-1) can be present in the form of various regioisomers. For example in the form of mixtures of compounds having the definition Q62 or Q63 or in the form of mixtures of Q58 and Q59. Accordingly, the invention also embraces active compound combinations comprising mixtures of compounds of the formula (I-1) where $Q_Y$ has the meanings Q62 and Q63, and also Q58 and Q59, and the compounds may be present in various mixing ratios, and one or more active compounds from group (II). Preference is given here to mixing ratios of compounds of the formula (I) In which the radical $Q_Y$ represents Q62 or Q58 to compounds of the formula (I) in which the radical Qy represents Q63 or Q59 of from 60;40 to 99:1, particularly preferably from 70:30 to 97:3, very particularly preferably from 80:20 to 95:5. Special preference is given to the following mixing ratios of a compound of the formula (I) where $Q_Y$ has the meaning Q62 or Q58 to a compound of the formula (I) where $Q_Y$ has the meaning Q63 or Q59: 80:20; 81:19; 82;18; 83:17; 84;16; 85:15, 86:14; 87:13; 88:12; 89:11; 90:10, 91:9; 92:8; 93:7; 96:6; 95:5.

Preference is furthermore given to active compound combinations comprising at least one active compound of the general formula (I) or (I-1) and an active compound of group (II) selected from the group consisting of
bitertanol
bixafen
carpropamid
fenamidone
fluopicolide
fluopyram
fluoxastrobin
fluquinconazole
isotianil
metominostrobin
pencycuron
penflufen
prochloraz
propamocarb
propineb
prothioconazole
spiroxamine
tebuconazole
triadimenol
triazoxide
trifloxystrobin
ametoctradin
azoxystrobin
benthiavalicarb
boscalid
carbendazim
carboxin
chlorothalonil
cymoxanil
cyproconazole
cyprodinil
cyazofamid
difenoconazole
dimoxystrobin
epoxiconazole
fenpropidin
ferimzone
fluazinam
fludioxonil
flutolanil
flutriafol
fluxapyroxad
gentamycin
hymexazol
imazalil
ipconazole
isoprothiolane
isopyrazam
kasugamycin
mancozeb
mandipropamid
maneb
mefenoxam
metalaxyl
metconazole
metrafenone
orysastrobin
penthiopyrad
picoxystrobin
probenazole
propiconazole
proquinazid
pyraclostrobin
pyrimethanil
pyroquilon
quinoxyfen
sedaxane
tetraconazole
thiophanate-methyl
thiram
tolclofos-methyl
tricyclazole
tritconazole
validamycin
fosetyl-aluminium.

Particular preference is furthermore given to active compound combinations comprising at least one active compound of the general formula (I) or (I-1) and an active compound of group (II) selected from the group consisting of
bitertanol
bixafen
carpropamid
fenamidone
fluopicolide
fluopyram
fluoxastrobin
fluquinconazole
isotianil
metominostrobin
pencycuron
penflufen
prochloraz
propamocarb
propineb
prothioconazole
spiroxamine
tebuconazole
triadimenol
triazoxide
trifloxystrobin
fludioxonil
ipconazole
imazalil mancozeb
metalaxyl
mefenoxam
sedaxane
azoxystrobin
orysastrobin
carbendazim
boscalid
flutolanil
fluxapyroxad
fosetyl-aluminium
Very particular preference is given to active compound combinations comprising exactly one active compound of the formulae (I-1-1) to (I-1-60) and one or more active compounds of group (II).
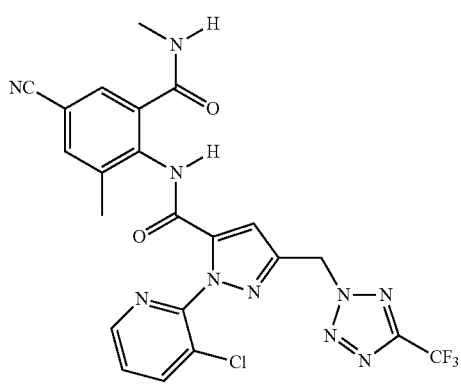
(I-1-1)
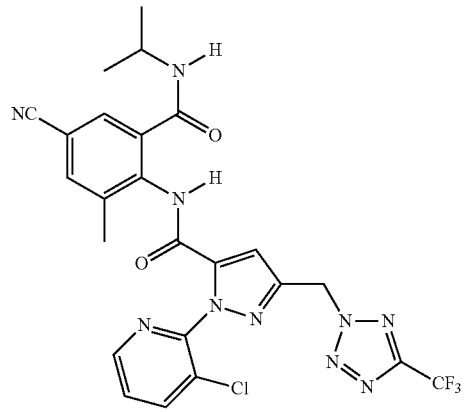
(I-1-4)
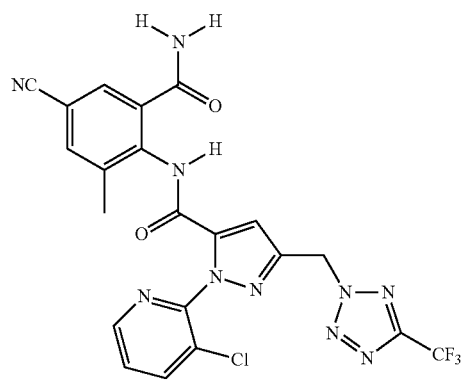
(I-1-5)
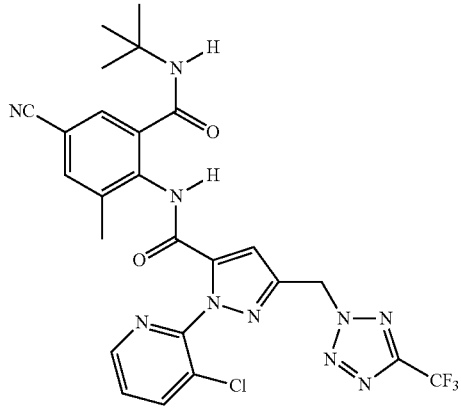
(I-1-2)
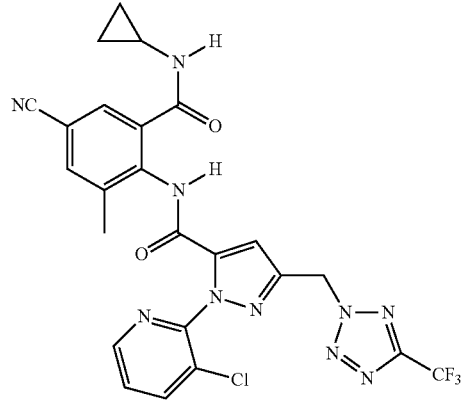
(I-1-6)
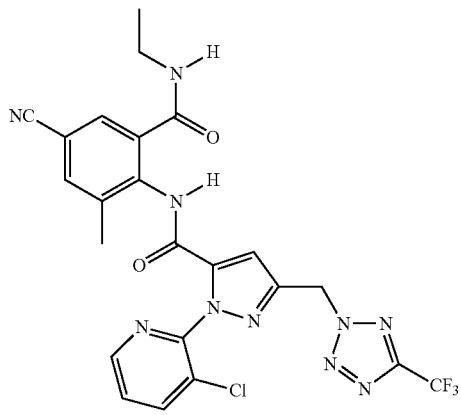
(I-1-3)
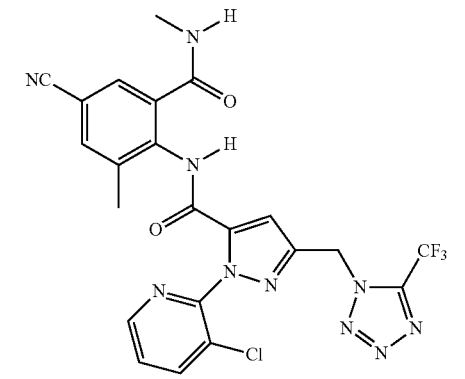
(I-1-7)

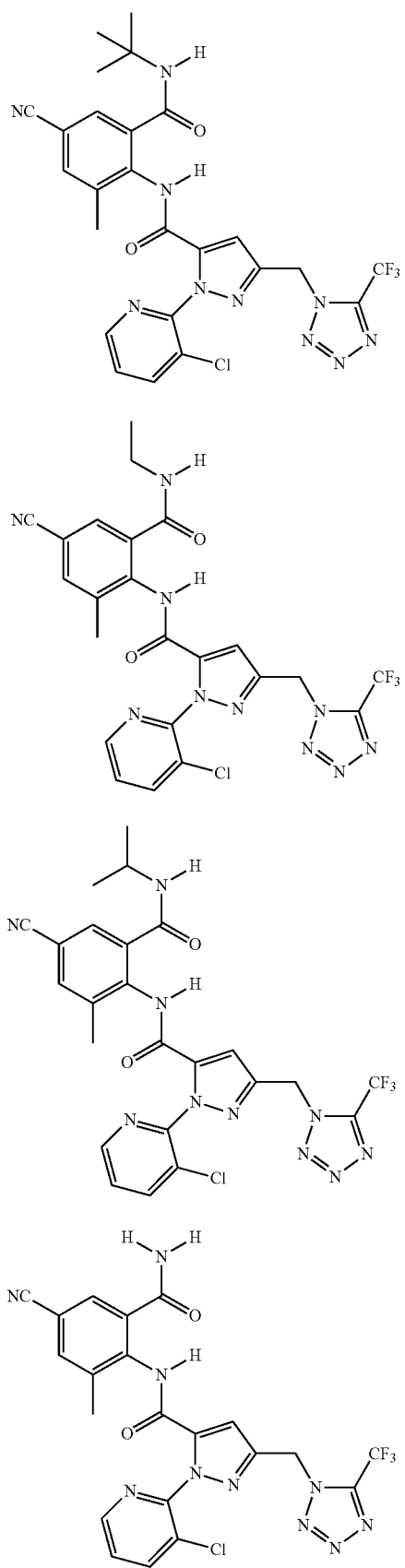
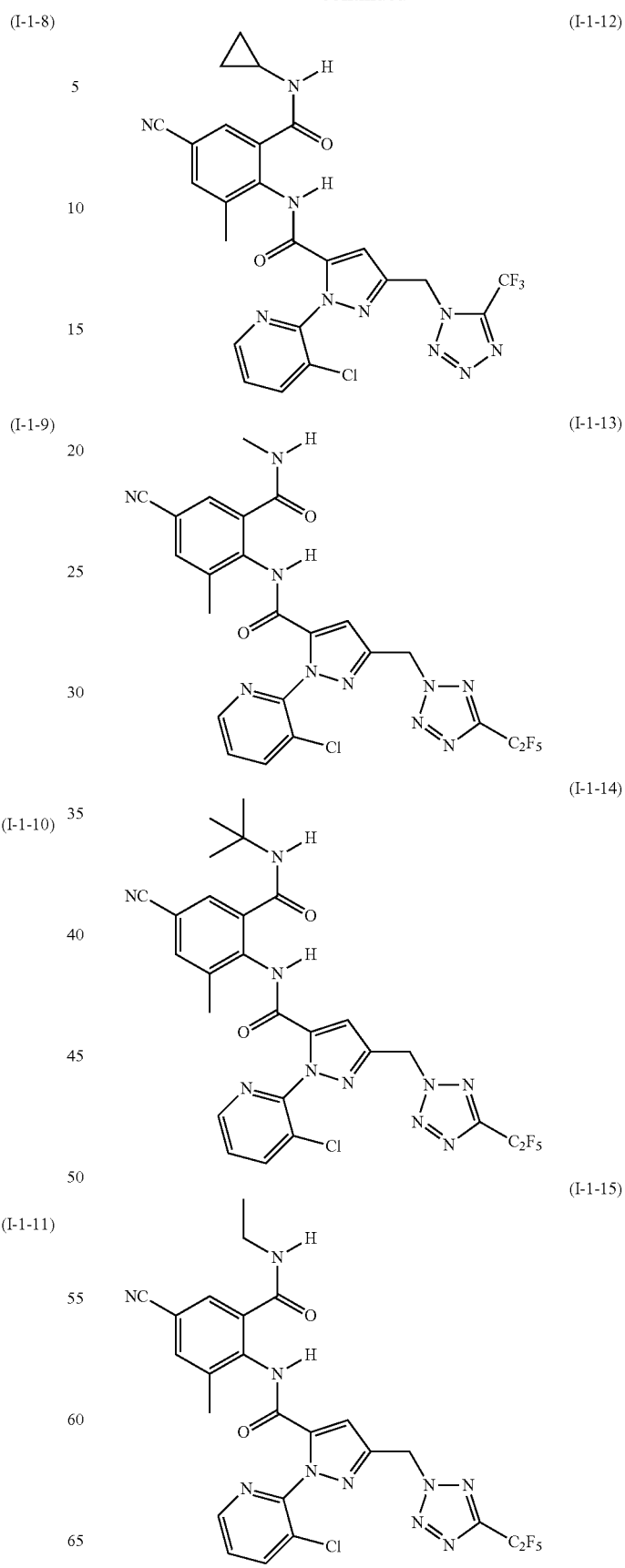

(I-1-16) 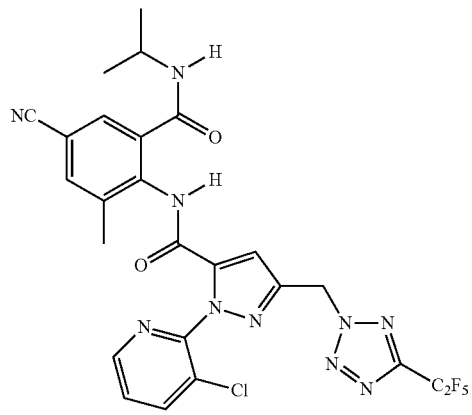
(I-1-17) 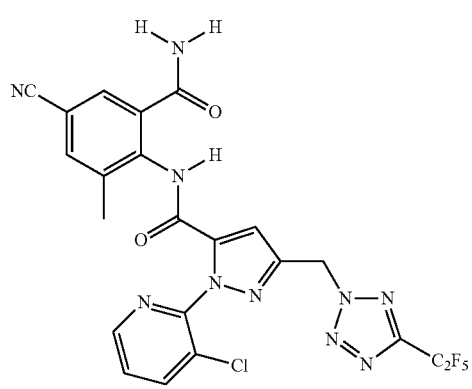
(I-1-18) 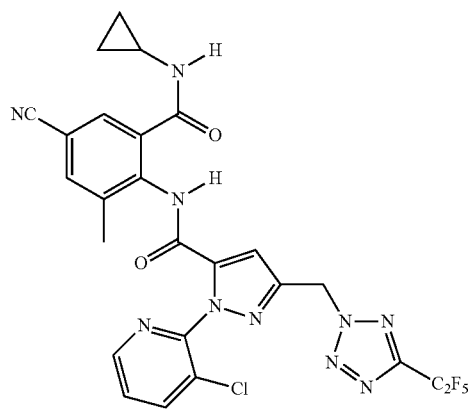
(I-1-19) 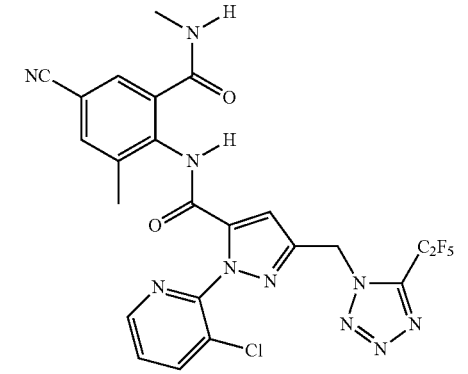
(I-1-20) 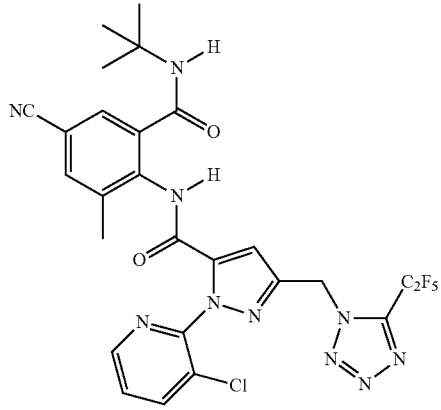
(I-1-21) 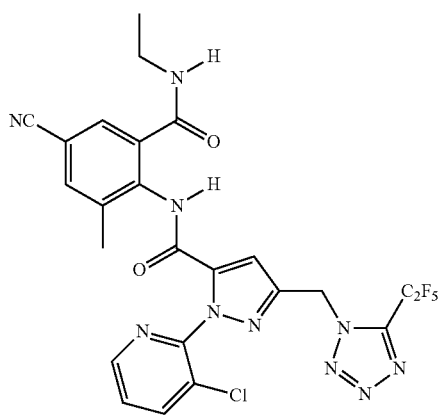
(I-1-22) 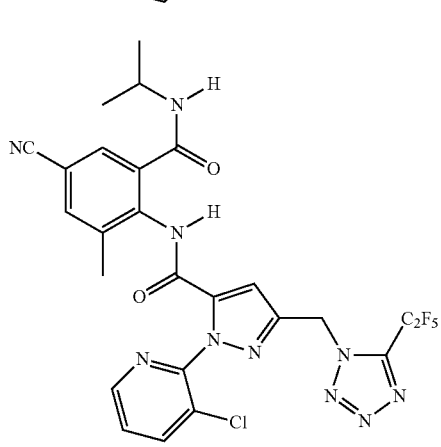
(I-1-23) 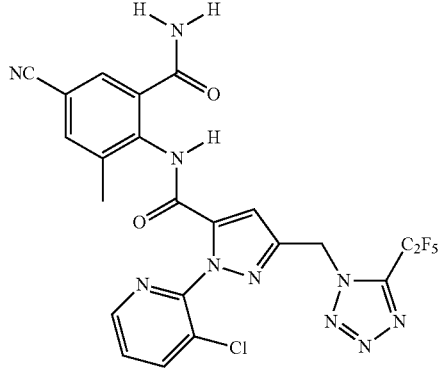

-continued
(I-1-24)
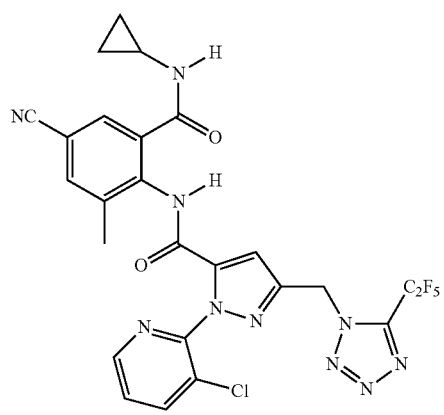
(I-1-25)
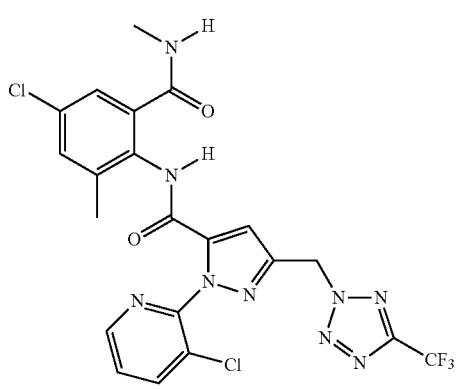
(I-1-26)
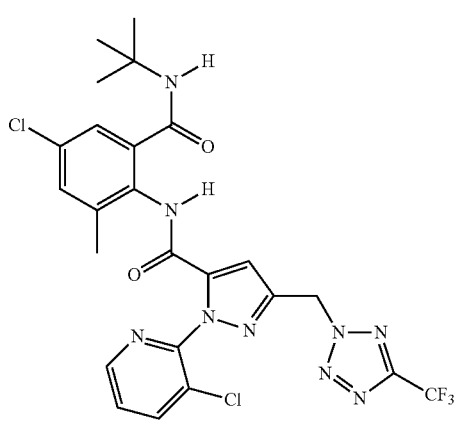
(I-1-27)
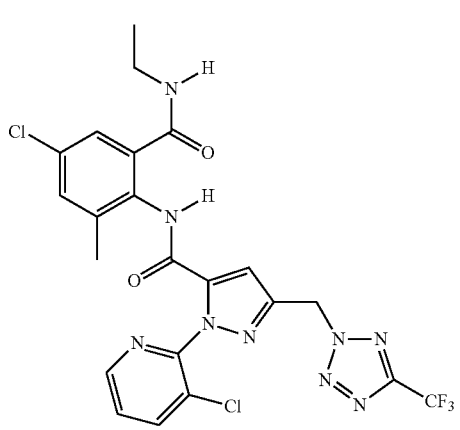
(I-1-28)
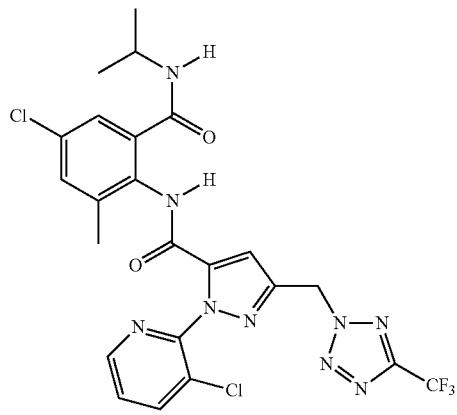
(I-1-29)
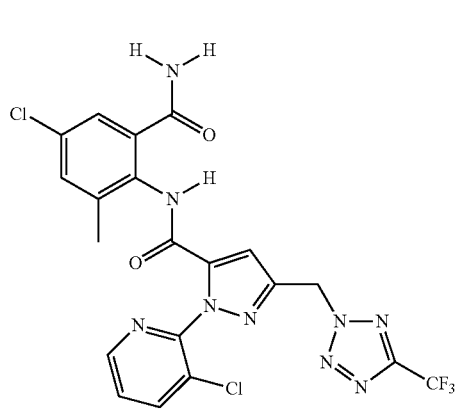
(I-1-30)
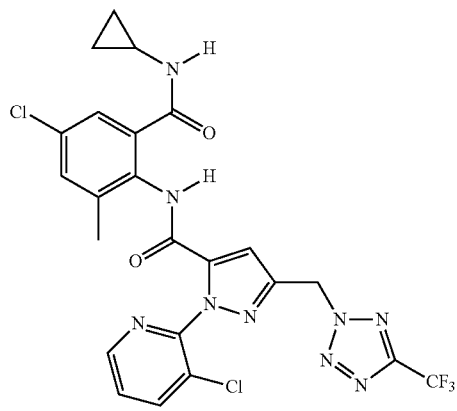
(I-1-31)
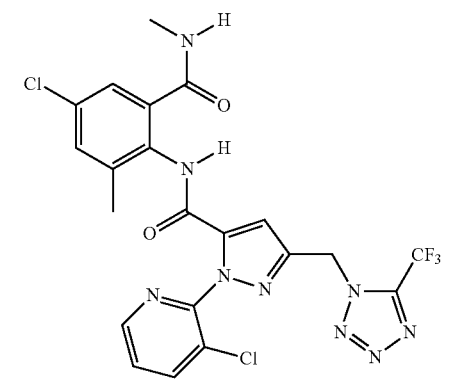

(I-1-32)
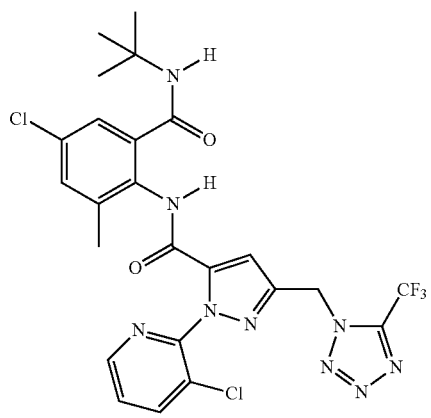
(I-1-33)
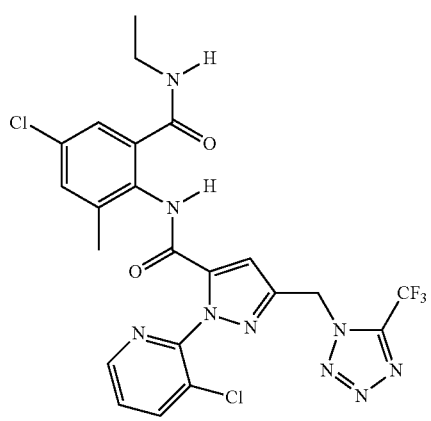
(I-1-34)
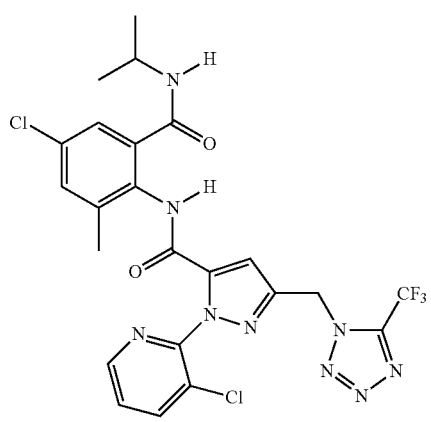
(I-1-35)
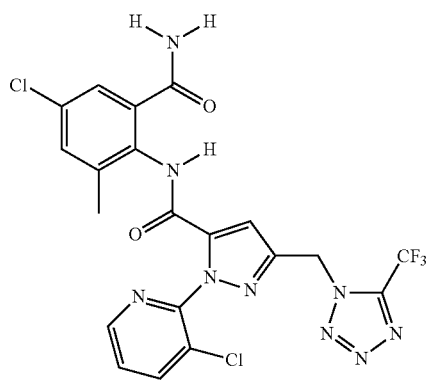
(I-1-36)
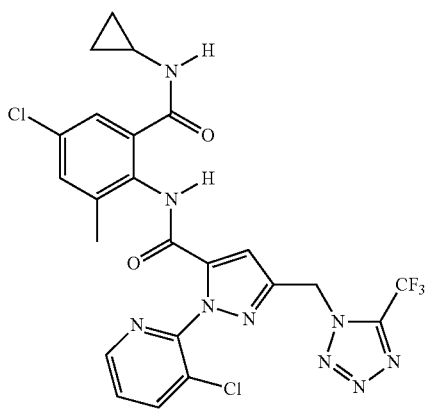
(I-1-37)
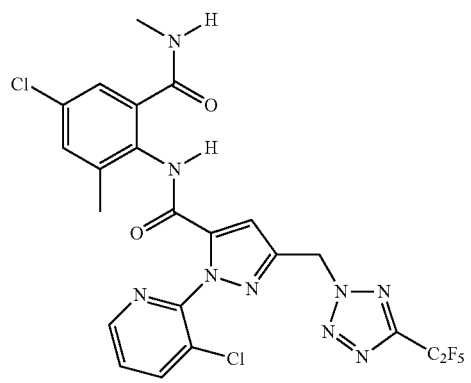
(I-1-38)
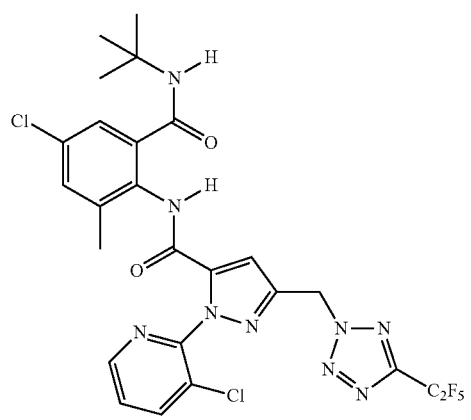
(I-1-39)
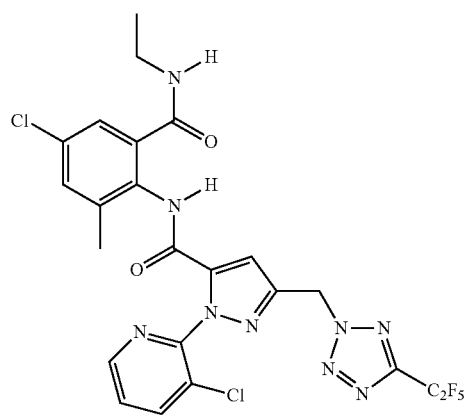

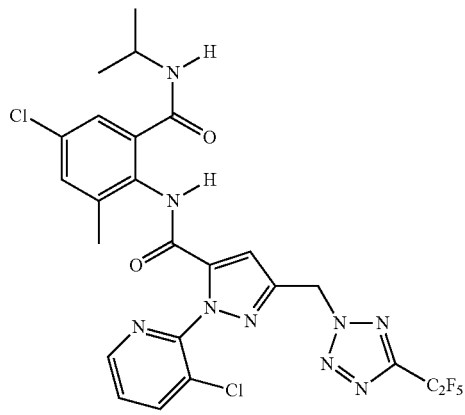
(I-1-40)
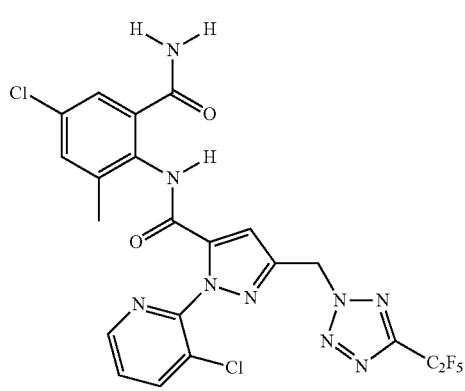
(I-1-41)
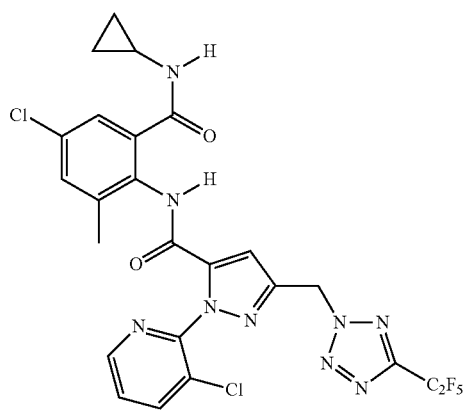
(I-1-42)
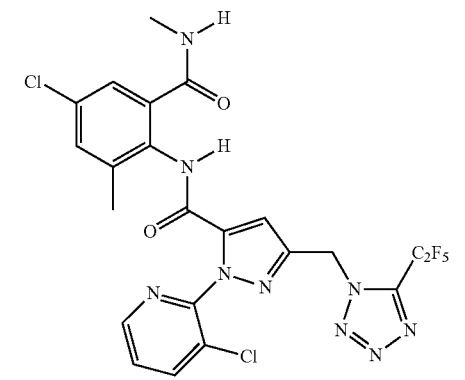
(I-1-43)
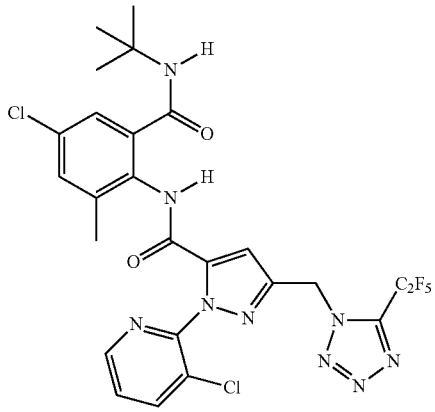
(I-1-44)
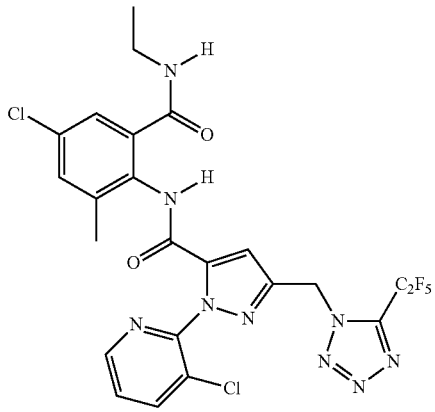
(I-1-45)
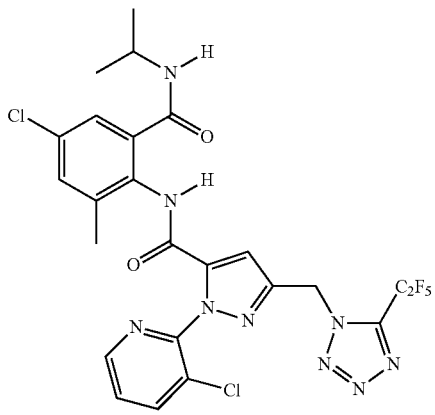
(I-1-46)
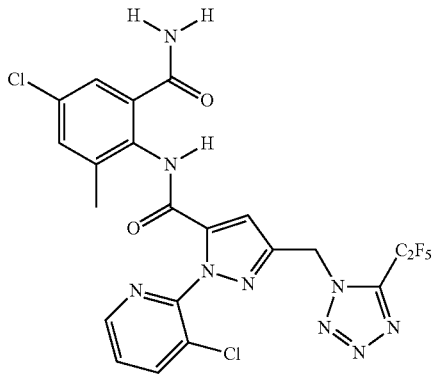
(I-1-47)

-continued
(I-1-48)
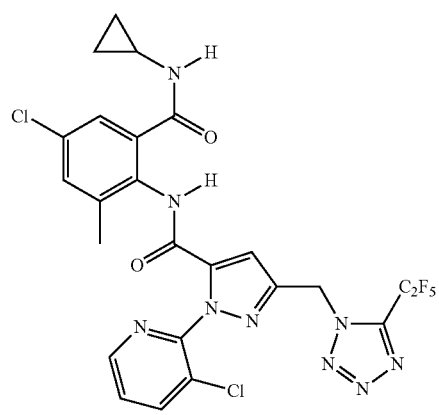
(I-1-49)
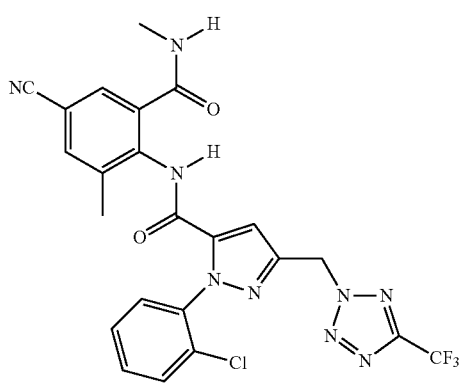
(I-1-50)
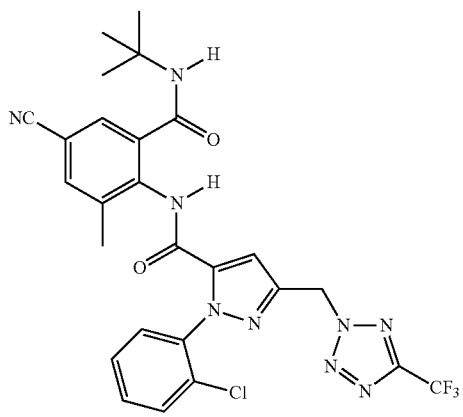
(I-1-51)
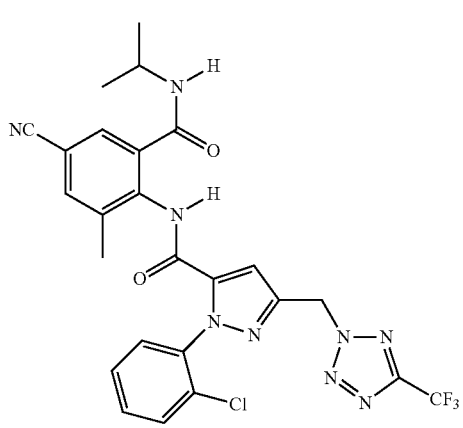
-continued
(I-1-52)
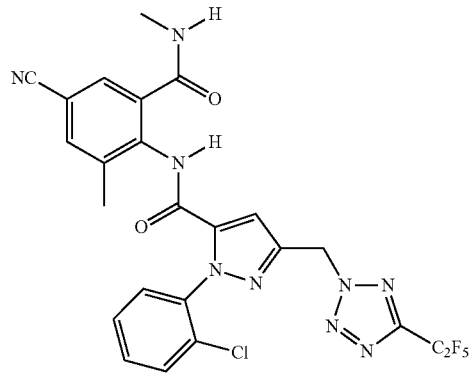
(I-1-53)
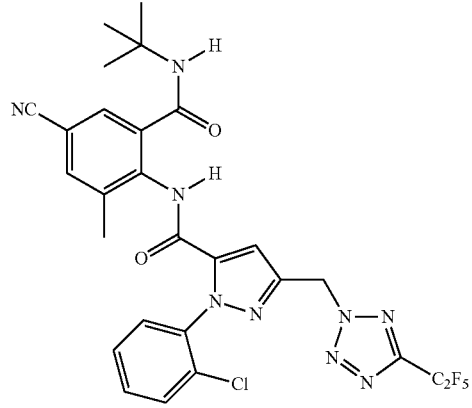
(I-1-54)
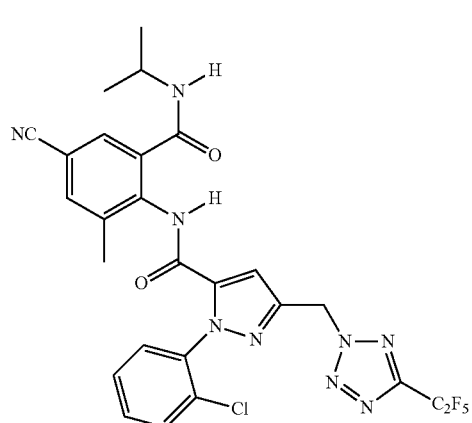
(I-1-55)
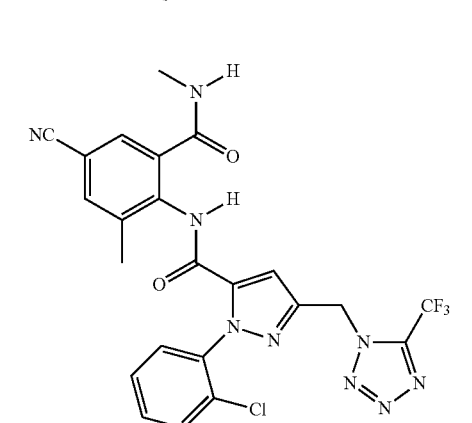

Very particular preference is furthermore given to active compound combinations comprising the mixtures given below of active compounds of the formulae (I-1-1) to (I-1-60) and one or more active compounds of group (II).

These mixtures are preferably present in a mixing ratio of from 80:20 to 99:1. In an exemplary manner, mention may be made of the mixture I-1-1/I-1-7, where the compound of the formula I-1-1 and the compound of the formula I-1-7 are present in a mixing ratio from 80:20 to 99:1, In an exemplary manner, mention may also be made of the mixture I-1-2/I-1-8, where the compound of the formula I-1-2 and the compound of the formula I-1-8 are present in a mixing ratio from 80:20 to 99:1.

I-1-1/I-1-7,
I-1-2/I-1-8,
I-1-3/I-1-9,
I-1-4/I-1-10,
I-1-5/I-1-11,
I-1-6/I-1-12,
I-1-13/I-1-19,
I-1-14/I-1-20,
I-1-15/I-1-21,
I-1-16/I-1-22,
I-1-17/I-1-23,
I-1-18/I-1-24,
I-1-25/I-1-31,
I-1-26/I-1-32,
I-1-27/I-1-33,
I-1-28/I-1-34,
I-1-29/I-1-35,
I-1-30/I-1-36,
I-1-37/I-1-43,
I-1-38/I-1-44,
I-1-39/I-1-45,
I-1-40/I-1-46,
I-1-41/I-1-47,
I-1-42/I-1-48,
I-1-49/I-1-55,
I-1-50/I-1-56,
I-1-51/I-1-57,
I-1-52/I-1-58,
I-1-53/I-1-59,
I-1-54/I-1-60.

Especially preferred are combinations comprising the active compound (I-1-1) and exactly one active compound of group II in the mixing ratios given in Table 1.

Especially preferred are combinations comprising the active compound (I-1-2) and exactly one active compound of group II in the mixing ratios given in Table 1.

Especially preferred are combinations comprising the active compound (I-1-3) and exactly one active compound of group II in the mixing ratios given in Table 1.

Especially preferred are combinations comprising the active compound (I-1-4) and exactly one active compound of group II in the mixing ratios given in Table 1.

Especially preferred are combinations comprising the active compound (I-1-5) and exactly one active compound of group II in the mixing ratios given in Table 1.

Especially preferred are combinations comprising the active compound (I-1-6) and exactly one active compound of group II in the mixing ratios given in Table 1.

Especially preferred are combinations comprising the active compound (I-1-7) and exactly one active compound of group II in the mixing ratios given in Table 1.

Especially preferred are combinations comprising the active compound (I-1-8) and exactly one active compound of group II in the mixing ratios given in Table 1.

Especially preferred are combinations comprising the active compound (I-1-9) and exactly one active compound of group II in the mixing ratios given in Table 1.

Especially preferred are combinations comprising the active compound (I-1-10) and exactly one active compound of group II in the mixing ratios given in Table 1.

Especially preferred are combinations comprising the active compound (I-1-11) and exactly one active compound of group II in the mixing ratios given in Table 1.

Especially preferred are combinations comprising the active compound (I-1-12) and exactly one active compound of group II in the mixing ratios given in Table 1.

Especially preferred are combinations comprising the active compound (I-1-13) and exactly one active compound of group II in the mixing ratios given in Table 1.

Especially preferred are combinations comprising the active compound (I-1-14) and exactly one active compound of group II in the mixing ratios given in Table 1.

Especially preferred are combinations comprising the active compound (I-1-15) and exactly one active compound of group II in the mixing ratios given in Table 1.

Especially preferred are combinations comprising the active compound (I-1-16) and exactly one active compound of group II in the mixing ratios given in Table 1.

Especially preferred are combinations comprising the active compound (I-1-17) and exactly one active compound of group II in the mixing ratios given in Table 1.

Especially preferred are combinations comprising the active compound (I-1-18) and exactly one active compound of group II in the mixing ratios given in Table 1.

Especially preferred are combinations comprising the active compound (I-1-19) and exactly one active compound of group II in the mixing ratios given in Table 1.

Especially preferred are combinations comprising the active compound (I-1-20) and exactly one active compound of group II in the mixing ratios given in Table 1.

Especially preferred are combinations comprising the active compound (I-1-21) and exactly one active compound of group II in the mixing ratios given in Table 1.

Especially preferred are combinations comprising the active compound (I-1-22) and exactly one active compound of group II in the mixing ratios given in Table 1.

Especially preferred are combinations comprising the active compound (I-1-23) and exactly one active compound of group II in the mixing ratios given in Table 1.

Especially preferred are combinations comprising the active compound (I-1-24) and exactly one active compound of group II in the mixing ratios given in Table 1.

Especially preferred are combinations comprising the active compound (I-1-25) and exactly one active compound of group II in the mixing ratios given in Table 1.

Especially preferred are combinations comprising the active compound (I-1-26) and exactly one active compound of group II in the mixing ratios given in Table 1.

Especially preferred are combinations comprising the active compound (I-1-27) and exactly one active compound of group II in the mixing ratios given in Table 1.

Especially preferred are combinations comprising the active compound (I-1-28) and exactly one active compound of group II in the mixing ratios given in Table 1.

Especially preferred are combinations comprising the active compound (I-1-29) and exactly one active compound of group II in the mixing ratios given in Table 1.

Especially preferred are combinations comprising the active compound (I-1-30) and exactly one active compound of group II in the mixing ratios given in Table 1.

Especially preferred are combinations comprising the active compound (I-1-31) and exactly one active compound of group II in the mixing ratios given in Table 1.

Especially preferred are combinations comprising the active compound (I-1-32) and exactly one active compound of group II in the mixing ratios given in Table 1.

Especially preferred are combinations comprising the active compound (I-1-32) and exactly one active compound of group II in the mixing ratios given in Table 1.

Especially preferred are combinations comprising the active compound (I-1-34) and exactly one active compound of group II in the mixing ratios given in Table 1.

Especially preferred are combinations comprising the active compound (I-1-35) and exactly one active compound of group II in the mixing ratios given in Table 1.

Especially preferred are combinations comprising the active compound (I-1-36) and exactly one active compound of group II in the mixing ratios given in Table 1.

Especially preferred are combinations comprising the active compound (I-1-37) and exactly one active compound of group II in the mixing ratios given in Table 1.

Especially preferred are combinations comprising the active compound (I-1-38) and exactly one active compound of group II in the mixing ratios given in Table 1.

Especially preferred are combinations comprising the active compound (I-1-39) and exactly one active compound of group II in the mixing ratios given in Table 1.

Especially preferred are combinations comprising the active compound (I-1-40) and exactly one active compound of group II in the mixing ratios given in Table 1.

Especially preferred are combinations comprising the active compound (I-1-41) and exactly one active compound of group II in the mixing ratios given in Table 1.

Especially preferred are combinations comprising the active compound (I-1-42) and exactly one active compound of group II in the mixing ratios given in Table 1.

Especially preferred are combinations comprising the active compound (I-1-43) and exactly one active compound of group II in the mixing ratios given in Table 1.

Especially preferred are combinations comprising the active compound (I-1-44) and exactly one active compound of group II in the mixing ratios given in Table 1.

Especially preferred are combinations comprising the active compound (I-1-45) and exactly one active compound of group II in the mixing ratios given in Table 1.

Especially preferred are combinations comprising the active compound (I-1-46) and exactly one active compound of group II in the mixing ratios given in Table 1.

Especially preferred are combinations comprising the active compound (I-1-47) and exactly one active compound of group II in the mixing ratios given in Table 1.

Especially preferred are combinations comprising the active compound (I-1-48) and exactly one active compound of group II in the mixing ratios given in Table 1.

Especially preferred are combinations comprising the active compound (I-1-49) and exactly one active compound of group II in the mixing ratios given in Table 1.

Especially preferred are combinations comprising the active compound (I-1-50) and exactly one active compound of group II in the mixing ratios given in Table 1.

Especially preferred are combinations comprising the active compound (I-1-51) and exactly one active compound of group II in the mixing ratios given in Table 1.

Especially preferred are combinations comprising the active compound (I-1-52) and exactly one active compound of group II in the mixing ratios given in Table 1.

Especially preferred are combinations comprising the active compound (I-1-53) and exactly one active compound of group II in the mixing ratios given in Table 1.

Especially preferred are combinations comprising the active compound (I-1-54) and exactly one active compound of group II in the mixing ratios given in Table 1.

Especially preferred are combinations comprising the active compound (I-1-55) and exactly one active compound of group II in the mixing ratios given in Table 1.

Especially preferred are combinations comprising the active compound (I-1-56) and exactly one active compound of group II in the mixing ratios given in Table 1.

Especially preferred are combinations comprising the active compound (I-1-57) and exactly one active compound of group II in the mixing s given in Table 1.

Especially preferred are combinations comprising the active compound (I-1-58) and exactly one active compound of group II in the mixing ratios given in Table 1.

Especially preferred are combinations comprising the active compound (I-1-59 and exactly one active compound of group II in the mixing ratios given in Table 1.

Especially preferred are combinations comprising the active compound (I-1-60) and exactly one active compound of group II in the mixing ratios given in Table 1.

In addition, the active compound combinations may also con vise other fungicidally, acaricidally or insecticidally active components for admixture.

If the active compounds are present in the active compound combinations according to the invention in certain weight ratios, the enhanced activity becomes evident. However, the weight ratios of the active compounds in the active compound combinations can be varied within a relatively wide range. In general, the combinations according to the invention comprise active compounds of the formula (I) to mixing partner of group (II) in a ratio from 625:1 to 1:625; preferably in the preferred and particularly preferred mixing ratios listed in Table 1 below:

the mixing ratios are based on weight ratios. The ratio is to be understood as active compound of the formula (I): mixing partner to formula (I): mixing partner

TABLE 1

| Mixing partner | preferred mixing ratio | particularly preferred mixing ratio | very particularly preferred mixing ratio |
|---|---|---|---|
| bitertanol | 625:1 to 1:625 | 125:1 to 1:125 | 25:1 to 1:25 |
| bixafen | 625:1 to 1:625 | 125:1 to 1:125 | 25:1 to 1:25 |
| carpropamid | 625:1 to 1:625 | 125:1 to 1:125 | 25:1 to 1:25 |
| fenamidone | 625:1 to 1:625 | 125:1 to 1:125 | 25:1 to 1:25 |
| fosetyl-aluminium | 625:1 to 1:625 | 125:1 to 1:125 | 25:1 to 1:25 |
| fluopicolide | 625:1 to 1:625 | 125:1 to 1:125 | 25:1 to 1:25 |
| fluopyram | 625:1 to 1:625 | 125:1 to 1:125 | 25:1 to 1:25 |
| fluoxastrobin | 625:1 to 1:625 | 125:1 to 1:125 | 25:1 to 1:25 |
| fluquinconazole | 625:1 to 1:625 | 125:1 to 1:125 | 25:1 to 1:25 |
| isotianil | 625:1 to 1:625 | 125:1 to 1:125 | 25:1 to 1:25 |
| metominostrobin | 625:1 to 1:625 | 125:1 to 1:125 | 25:1 to 1:25 |
| pencycuron | 625:1 to 1:625 | 125:1 to 1:125 | 25:1 to 1:25 |
| penflufen | 625:1 to 1:625 | 125:1 to 1:125 | 25:1 to 1:25 |
| prochloraz | 625:1 to 1:625 | 125:1 to 1:125 | 25:1 to 1:25 |
| propamocarb | 625:1 to 1:625 | 125:1 to 1:125 | 25:1 to 1:25 |
| propineb | 625:1 to 1:625 | 125:1 to 1:125 | 25:1 to 1:25 |
| prothioconazole | 625:1 to 1:625 | 125:1 to 1:125 | 25:1 to 1:25 |
| spiroxamine | 625:1 to 1:625 | 125:1 to 1:125 | 25:1 to 1:25 |
| tebuconazole | 625:1 to 1:625 | 125:1 to 1:125 | 25:1 to 1:25 |
| triadimenol | 625:1 to 1:625 | 125:1 to 1:125 | 25:1 to 1:25 |
| triazoxide | 625:1 to 1:625 | 125:1 to 1:125 | 25:1 to 1:25 |
| trifloxystrobin | 625:1 to 1:625 | 125:1 to 1:125 | 25:1 to 1:25 |
| ametoctradin | 625:1 to 1:625 | 125:1 to 1:125 | 25:1 to 1:25 |
| azoxystrobin | 625:1 to 1:625 | 125:1 to 1:125 | 25:1 to 1:25 |
| benthiavalicarb | 625:1 to 1:625 | 125:1 to 1:125 | 25:1 to 1:25 |
| boscalid | 625:1 to 1:625 | 125:1 to 1:125 | 25:1 to 1:25 |
| carbendazim | 625:1 to 1:625 | 125:1 to 1:125 | 25:1 to 1:25 |
| carboxin | 625:1 to 1:625 | 125:1 to 1:125 | 25:1 to 1:25 |
| chlorothalonil | 625:1 to 1:625 | 125:1 to 1:125 | 25:1 to 1:25 |
| cymoxanil | 625:1 to 1:625 | 125:1 to 1:125 | 25:1 to 1:25 |
| cyproconazole | 625:1 to 1:625 | 125:1 to 1:125 | 25:1 to 1:25 |
| cyprodinil | 625:1 to 1:625 | 125:1 to 1:125 | 25:1 to 1:25 |
| cyazofamid | 625:1 to 1:625 | 125:1 to 1:125 | 25:1 to 1:25 |
| difenoconazole | 625:1 to 1:625 | 125:1 to 1:125 | 25:1 to 1:25 |
| dimoxystrobin | 625:1 to 1:625 | 125:1 to 1:125 | 25:1 to 1:25 |
| epoxiconazole | 625:1 to 1:625 | 125:1 to 1:125 | 25:1 to 1:25 |
| fenpropidin | 625:1 to 1:625 | 125:1 to 1:125 | 25:1 to 1:25 |
| ferimzone | 625:1 to 1:625 | 125:1 to 1:125 | 25:1 to 1:25 |
| fluazinam | 625:1 to 1:625 | 125:1 to 1:125 | 25:1 to 1:25 |
| fludioxonil | 625:1 to 1:625 | 125:1 to 1:125 | 25:1 to 1:25 |
| flutolanil | 625:1 to 1:625 | 125:1 to 1:125 | 25:1 to 1:25 |
| Flutriafol | 625:1 to 1:625 | 125:1 to 1:125 | 25:1 to 1:25 |
| fluxapyroxad | 625:1 to 1:625 | 125:1 to 1:125 | 25:1 to 1:25 |
| gentamycin | 625:1 to 1:625 | 125:1 to 1:125 | 25:1 to 1:25 |
| hymexazol | 625:1 to 1:625 | 125:1 to 1:125 | 25:1 to 1:25 |
| imazalil | 625:1 to 1:625 | 125:1 to 1:125 | 25:1 to 1:25 |
| ipconazole | 625:1 to 1:625 | 125:1 to 1:125 | 25:1 to 1:25 |
| isoprothiolane | 625:1 to 1:625 | 125:1 to 1:125 | 25:1 to 1:25 |
| isopyrazam | 625:1 to 1:625 | 125:1 to 1:125 | 25:1 to 1:25 |
| kasugamycin | 625:1 to 1:625 | 125:1 to 1:125 | 25:1 to 1:25 |
| mancozeb | 625:1 to 1:625 | 125:1 to 1:125 | 25:1 to 1:25 |
| mandipropamid | 625:1 to 1:625 | 125:1 to 1:125 | 25:1 to 1:25 |
| maneb | 625:1 to 1:625 | 125:1 to 1:125 | 25:1 to 1:25 |
| mefenoxam | 625:1 to 1:625 | 125:1 to 1:125 | 25:1 to 1:25 |
| metalaxyl | 625:1 to 1:625 | 125:1 to 1:125 | 25:1 to 1:25 |
| metconazole | 625:1 to 1:625 | 125:1 to 1:125 | 25:1 to 1:25 |
| metrafenone | 625:1 to 1:625 | 125:1 to 1:125 | 25:1 to 1:25 |
| orysastrobin | 625:1 to 1:625 | 125:1 to 1:125 | 25:1 to 1:25 |
| penthiopyrad | 625:1 to 1:625 | 125:1 to 1:125 | 25:1 to 1:25 |
| picoxystrobin | 625:1 to 1:625 | 125:1 to 1:125 | 25:1 to 1:25 |
| probenazole | 625:1 to 1:625 | 125:1 to 1:125 | 25:1 to 1:25 |
| propiconazole | 625:1 to 1:625 | 125:1 to 1:125 | 25:1 to 1:25 |
| proquinazid | 625:1 to 1:625 | 125:1 to 1:125 | 25:1 to 1:25 |
| pyraclostrobin | 625:1 to 1:625 | 125:1 to 1:125 | 25:1 to 1:25 |
| pyrimethanil | 625:1 to 1:625 | 125:1 to 1:125 | 25:1 to 1:25 |
| pyroquilon | 625:1 to 1:625 | 125:1 to 1:125 | 25:1 to 1:25 |
| quinoxyfen | 625:1 to 1:625 | 125:1 to 1:125 | 25:1 to 1:25 |
| sedaxane | 625:1 to 1:625 | 125:1 to 1:125 | 25:1 to 1:25 |
| tetraconazole | 625:1 to 1:625 | 125:1 to 1:125 | 25:1 to 1:25 |
| thiophanate-methyl | 625:1 to 1:625 | 125:1 to 1:125 | 25:1 to 1:25 |
| thiram | 625:1 to 1:625 | 125:1 to 1:125 | 25:1 to 1:25 |
| tolclofos-methyl | 625:1 to 1:625 | 125:1 to 1:125 | 25:1 to 1:25 |
| tricyclazole | 625:1 to 1:625 | 125:1 to 1:125 | 25:1 to 1:25 |
| triticonazole | 625:1 to 1:625 | 125:1 to 1:125 | 25:1 to 1:25 |
| validamycin | 625:1 to 1:625 | 125:1 to 1:125 | 25:1 to 1:25 |

When using the active compound combinations according to the invention as fungicides, insecticides or acaricides, the application rates can be varied within a relatively wide range, depending on the kind of application. The application rate of the active compound combinations according to the invention is when treating plant parts, e.g. leaves: from 0.1 to 1000 g/ha, preferably from 10 to 500 g/ha, particularly preferably from 50 to 300 g/ha (when the application is carried out by watering or dripping, it may even be possible to reduce the application rate, in particular when inert substrates such as rock wool or perlite are used); when treating seed: from 1 to 2000 g per 100 kg of seed, preferably from 2 to 1000 g per 100 kg of seed, particularly preferably from 3 to 750 g per 100 kg of seed, very particularly preferably from 5 to 500 g per 100 kg of seed; when treating the soil: from 0.1 to 5000 g/ha, preferably from 1 to 1000 g/ha.

These application rates are mentioned only by way of example and are not limiting the sense of the invention.

The active compound combinations according to the invention can be employed for protecting plants for a certain period of time after treatment against attack by phytopathogenic fungi and/or animal pests. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

The active compound combinations according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling phytopathogenic fungi such as *Plasmodiophoromycetes, Oomycetes, Chytridiomycetes, Zygomycetes, Ascomycetes, Basidiomycetes, Deuteromycetes* etc. and animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development.

The active compound combinations according to the invention have a very good fungicidal activity and can be employed for controlling phytopathogenic fungi such as *Plasmodiophoromyeetes, Oomycetes, Chytridiontycetes, Zygomycetes, Ascomycetes, Basidiomycetes, Deuteromycetes* and the like.

The active compound combinations according to the invention are particularly suitable for controlling *Phytophthora infestans, Plasmopara viticola* and *Botrytis cinerea*.

Some pathogens causing fungal and bacterial diseases which con er the generic names listed above may be mentioned as examples, but not by way of limitation:

Fungicides can be employed in crop protection for controlling Plasmodiophoromycetes, Oomycetes, Chytridiornycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

diseases caused by powdery mildew pathogens, such as, for example,

*Blumeria* species, such as, for example, *Blurneria graminis;*

*Podosphaera* species, for example *Podosphaera leucotricha;*

*Sphaerotheca* species, for example *Sphaerotheca fuliginea;*

*Uncinula* species, such as, for example, *Uncinula necator;* diseases caused by rust disease pathogens, such as, for example,

*Gymnosporangium* species, such as, for example, *Gymnosporangium sabinae*

*Hemileia* species, such s for example *Hemileia vastatrix,*

*Phakopsora* species, such as, for example, *Phakopsora pachyrhizi* and *Phakopsora meibomiae;*

*Puccinia* species, for example *Puccinia recondita;*

*Uromyces* species, for example *Uromyces appendiculatus* diseases caused by pathogens from the group of the Oomycetes, such as, for example,

*Bremia* species, for example *Bremia lactucae;*

*Peronospora* species, for example *Peronospora pisi* or *P. brassicae;*

*Phytophthora* species, for example *Phytophthora infestans;*

*Plasmopara* species, for example *Plasmopara viticola;*

*Pseudoperonospora* species, for example *Pseudoperonospora humuli* or

*Pseudoperonospora cubensis;*

*Pythium* species, for example *Pythium ultimum;* leaf blotch diseases and leaf wilt diseases caused, for example, by

*Alternaria* species, such as, for example, *Alternaria solani;*

*Cercospora* species, such as, for example, *Cercospora beticola;*

*Cladiosporum* species, such as, for example, *Cladiosporium cucumerinum;*

*Cochliobolus* species, such as, for example, *Cochliobolus sativus;*

(conidia form: Drechslera, syn: *Helminthosporium*);

*Colletotrichum* species, such as, for example, *Colletotrichum lindemuthanium;*

*Cycloconium* species, such as, for example, *Cycloconium oleaginum;*

*Diaporthe* species, such as, for example, *Diaporthe citri;*

*Eisinoe* species, such as, for example, *Elsinoe fawcettii;*

*Gloeosporium* species, such as, for example, *Gloeosporium laeticolor;*

*Glomerella* species, such as, for example, *Glomerella cingulata;*

*Guignardia* species, such as, for example, *Guignardia bidwelli;*

*Leptosphaeria* species, such as, for example, *Leptosphaeria maculans;*

*Magnaporthe* species, such as, for example, *Magnaporthe grisea;*

*Mycosphaerella* species, such as, for example, *Mycosphaerelle graminicola;*

*Phaeosphaeria* species, such as, for example, *Phaeosphaeria nodorum;*

*Pyrenophora* species, such as, for example, *Pyrenophora teres;*

*Ramularia* species, such as, for example, *Ramularia collo-cygni*;
*Rhynchosporium* species, such as, for example, *Rhynchosporium secalis*;
*Septoria* species, such as, for example, *Septoria apii*;
*Typhula* species, such as, for example, *Typhula incarnata*;
*Venturia* species, for example *Venturia inaequalis*;
root and stein diseases caused, for example, by
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example, *Rhizoctonia solani*;
*Tapesia* species, such as, for example, *Tapesia acuformis*;
*Thielaviopsis* species, such as, for example, *Thielaviopsis basicola*;
ear and panicle diseases (including maize cobs) caused, for example, by
*Altenaria* species, such as, for example, *Alternaria* spp.;
*Aspergillus* species, such as, for example, *Aspergillus flavus*;
*Cladosporium* species, such as, for example, *Cladosporium* spp.;
*Claviceps* species, such as, for example, *Claviceps purpurea*;
*Fusarium* species, for example *Fusarium culmorum*;
*Gibberella* species, such as, for example, *Gibberella zeae*;
*Monographella* species, such as, for example, *Monographella nivalis*;
diseases caused by smut fungi, such as, for example,
*Sphacelotheca* species, such as, for example, *Sphacelotheca reiliana*;
*Tilletia* species, for example *Tilletia caries*;
*Urocystis* species, such as, for example, *Urocystis occulta*;
*Ustilago* species such as, for example, *Ustilago nuda*;
fruit rot caused, for example, by
*Aspergillus* species, such as, for example, *Aspergillus flavus*;
*Botrytis* species, for example *Botrytis cinerea*;
*Penicillium* species, such as, for example, *Penicillium expansum*;
*Sclerotinia* species, for example *Sclerotinia sclerotiorum*;
*Verticilium* species, such as, for example, *Verticilium alboatrum*;
seed- and soil-borne rot and wilt diseases, and also diseases of seedlings, caused, for example, by
*Fusarium* species, for example *Fusarium culmorum*;
*Phytophthora* species, such as, for example, *Phytophthora cactorum*;
*Pythium* species, for example *Pythium ultimum*;
*Rhizoctonia* species, such as, for example, *Rhizoctonia solani*;
*Selerotium* species, such as, for example, *Selerotium rolfsii*;
cancerous diseases, galls and witches' broom caused, for example, by
*Nectria* species, such as, for example, *Nectria galligena*;
wilt diseases caused, for example, by
*Monilinia* species, such as, for example, *Monilinia laxa*;
deformations of leaves, flowers and fruits caused, for example, by
*Taphrina* species, such as, for example, *Taphrina deformans*;
degenerative diseases of woody plants caused, for example, by
*Esca* species, such as, for example, *Phaemoniella clamydospora*;
diseases of flowers and seeds caused, for example, by
*Botrytis* species, for example *Botrytis cinerea*;
diseases of plant tubers caused, for example, by
*Rhizoctonia* species, such as, for example, *Rhizoctonia solani*;
diseases caused by bacterial pathogens, such as, for example,
*Xanthomonas* species, for example *Xanthomonas campestris* pv. *oryzae*;
*Pseudomonas* species, for example *Pseudomonas syringae* pv. *lachrymans*;
*Erwinia* species, such as, for example, *Erwinia amylovora*.

Preference is given to controlling the following diseases of soya beans:
fungal diseases on leaves, sterns, pods and seeds caused, for example, by
artemaria leaf spot (*Alternaria* spec. atrans *tenuissima*), anthracnose (*Colletotrichum gioeosporoides* dematium var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*) frogeye leaf spot (*Cercospora sojina*), leptosphaerulina leaf spot (*Leptosphaerulina trifoiii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*).

Fungal diseases on roots and the stem base caused, for example, by
black root rot *Calonectria crotalariae*), charcoal rot (*Macrophomina phaseolina*), fusarium blight or wilt, root rot, and pod and collar rot (*Fusarium oxysporum, Fusarium orthoceras Fusarium semitectum, Fusarium equiseti*), mycoleptodiscus root rot (*Tvlycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermaturn, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*) sclerotinia southern blight (*Sclerotinia rolfsii*), thielaviopsis root rot (*Thielaviopsis basicola*).

The active compound combinations according to the invention can be employed particularly successfully for controlling cereal diseases such as, for example, against *Puccinia* species and diseases in viticulture and fruit and vegetable growing such as, for example, against *Botrytis, Venturia* or *Altemaria* species.

In addition, the active compound combinations according to the invention also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum, Aspergillus* species, such as *Aspergilius niger* and *Aspergillus fumigatus, Trichophyton* species, such as *Trichophyton mentagrophytes, Microsporon* species such as *Microsporon canis* and *audohinii*. The list of these fungi by no means constitutes a restriction of the mycotic spectrum covered, and is merely of illustrative character.

In addition, the active compound combinations according to the invention also have very good insecticidal activity. They have a very broad spectrum of insecticidal activity, in particular against the following animal pests:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example *Acalymma vittatum, Acanthoscelides obtectus, Adoretus* spp., *Agelastica aini, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagerms* spp., *Bruchidius obtectus, Bruchus* spp., *Cassida* spp., *Cerototma trifurcata, Ceutorrhynchus* spp., *Chaetocnema* spp., *Cleonus mendicus, Conoderus* spp., *Cosmopolites* spp., *Costelytra zealandica, Ctenicera* spp., *Curcolio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consannguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melelanotus* spp., *Meligethes aeneus, Melolontha* spp., *Migdoles* spp., *Monochamus* spp., *Naupactus xanthographus, Niptus hololeucus, Oryctes rhinoceros, Oryzaephilus surinamensis, Oryzaphagus olyzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus annatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora crythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stornoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Akcylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichina, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomina livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanca, Scotinophora* spp., *Stephanitis nashi, Tibraca* spp., *Triatoma* spp.

From the order of noptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Autlacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagula, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Per-*

*egrinus maidis, Phenacoccus* spp., *Phloeomyzus passerinii, Phorodon hamuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhkocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus* and *Porcellio scaber.*

From the order of the Isoptera, for example, *Acromyrmex* spp., *Atta* spp., *Cornitermes cumulans, Microtermes obesi, Odontotermes* spp., *Reticulitermes spp.*

From the order of the Lepidoptera, for example, *Acronicta major, Adoxophyes* spp., *Aedia leucomelas, Agrotis* spp., *Alabama* spp., *Amyelois transitella, Anarsia* spp., *Anticasia* spp., *Argyroploce* spp.,*Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp, *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Helothis* spp., *Hofinannophila pseudospretella, Homoeosoma* spp, *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp, *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stornopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella gerrnanica, Dichroplus* spp., *Gryllotalpa* spp., *Leucophae maderae, Locusta* spp., *Melanoplus* spp., *Periplaneta americana, Schistocerca gyegaria.*

From the order of the Siphonaptera, for example, *Ceratophyllus* spp. and *Xenopsylla cheopis.*

From the order of the Symphyla, for example, *Scutigerella* spp.

From the order of the Thysanoptera, for example *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

In the protection of materials, the active compound combinations according to the invention can be employed for protecting industrial materials against infection with, and destruction by, undesired microorganisms.

Industrial materials in the present context are understood to mean inanimate materials which have been prepared for use in industry. For example, industrial materials which are to be protected by inventive active compounds from microbial alteration or destruction may be adhesives, sizes, paper and cardboard, textiles, leather, wood, paints and plastic articles, cooling lubricants and other materials which can be infected with or destroyed by microorganisms. The range of materials to be protected also includes parts of production plants, for example cooling water circuits, which may be impaired by the proliferation of microorganisms. Industrial materials within the scope of the present invention preferably include adhesives, sizes, papers and cardboard, leather, wood, paints, cooling lubricants and heat transfer fluids, more preferably wood.

Microorganisms capable of degrading or altering the industrial materials include, for example, bacteria, fungi, yeasts, algae and slime organisms. The active compound combinations according to the invention preferably act against fungi, in particular moulds, wood-discolouring and wood-destroying fungi (Basidiomycetes), and against slime organisms and algae.

Examples include microorganisms of the following genera:

*Alternaria* such as *Alternaria tenuis,*
*Aspergillus* such as *Aspergillus niger,*
*Chaetomium* such as *Chaetomium globostan,*
*Coniophora* such as *Coniophora puetana,*
*Lentinus* such as *Lentinus tigrinus,*
*Penicillium* such as *Penicillium glaucum,*
*Polyporus* such as *Polyporus versicolor,*
*Aureobasidium* such as *Aureobasidium pullulans,*
*Sclerophoma* such as *Sclerophoma pityophila,*
*Trichoderma* such as *Trichoderma viride,*
*Escherichia* such as *Escherichia coli,*
*Pseudomonas* such as *Pseudomonas aeruginosa,* and
*Staphylococcus* such as *Staphylococcus aureus.*

Moreover, it has been found that the active compound combinations according to the invention show a potent insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Emobilis mollis, Priobium carpini, Lyctus brunneus, Lyctus afficanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus mimsrus.*

Dermapterans, such as *Sirex juvencus, Urocerus gigas, Urocerus gigas taignus, Urocerus augur.*

Termites, such as *Kalotermes flavicollis, Cryptotermes brevis, Heterotemes indicola, Reticulitermes flavipes, Reticulitermes santonensis, Reticulitermes lucifugus, Mastotermes darwiniensis, Zootermopsis nevadensis, Coptotermes formosanus.* bristletails, such as *Lepisma saccarina.*

Industrial materials in the present connection are understood to mean inanimate materials, such as preferably plastics, adhesives, sizes, papers and cards, leather, wood, processed wood products and coating compositions.

Most preferably, the material to be protected from insect infestation comprises wood and processed wood products.

Wood and processed wood products which can be protected by the active compound combinations according to the invention are to be understood as meaning, for example: building timber, wooden beams, railway sleepers, bridge components, boat jetties, wooden vehicles, boxes, pallets, containers, telegraph poles, wood panelling, wooden windows and doors,l txywood, chipboard, joinery or wooden products which are used quite generally in house-building or in building joinery.

The active compound combinations can be used as such, in the foil of concentrates or generally customary formulations such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal active compound combinations or concentrates used for the preservation of wood and wood-derived timber products comprise the active compound according to the invention in a concentration of 0.0001 to 95% by weight, in particular 0.001 to 60% by weight.

The amount of the active compound combinations or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

The active compound combinations are also suitable for controlling animal pests, especially insects, arachnids and mites, which are encountered in enclosed spaces, for example dwellings, factory hulls, offices, vehicle cabins and the like. They can be used in domestic insecticide products for controlling these pests. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Aranae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Isopiera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceurn.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The active compound combinations according to the invention are not only active against plant pests, hygiene pests and stored-product pests, but also in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, *Haematopinus* spp, *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp, *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylis* spp.

From the order of the Blattarida, for example *Blatta orientails, Periplaneta americana, Blattela germanica* and *Supella* spp.

From the subclass of the Acaria (Acarida) and the orders of the Meta- and Mesostigmata, for example *Argas* spp., *Ornithodorus* spp., *Otobius* spp, *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compound combinations according to the invention.

The active compound combinations according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoncal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, domestic animals and the like, the active compound combinations can be applied as foimulations (for example powders, emulsions, flowables) comprising the active compounds in an amount of 1 to 80% by weight, either directly or after 100- to 10 000-fold dilution, or they may be used as a chemical dip.

If appropriate, the active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*Mycoplasma*-like organisms) and RLO (*Rickettsia*-like organisms).

The present invention further relates to formulations and use forms prepared therefrom as crop protection compositions and/or pesticides, for example drench, drip and spray liquors, comprising at least one of the active compound combinations according to the invention. In some cases, the use forms comprise further crop protection compositions and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkyisiloxanes and/or salts, for example organic or inorganic ammonium or phosphonium salts, for example ammonium sulphate or diammonium hydrogenphosphate and/or retention promoters, for example dioetyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers-173, prepared by the FAO/WHO Joint Meeting on Pesticide Specifications, 2004, ISBN: 9251048576. The formulations optionally comprise, in addition to one or more active compounds according to the invention, further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are prepared in a known manner, for example by mixing the active compounds with auxiliaries such as, for example, extenders, solvents and/or solid carriers and/or further auxiliaries such as, for example, surfactants. The formulations are produced either in suitable plants or else before or during application.

Auxiliaries used may be substances capable of giving the formulation of the active compound, or the application forms prepared from these formulations (such as ready-touse crop protection compositions, for example, such as spray liquors or seed dressings) particular properties, such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters including fats and oils and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkyinaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic minerals such as finely divided silica, alumina and natural and synthetic silicates, resins, waxes and/or solid fertilizers, Mixtures of such carriers may also be used. Useful solid carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulphonic acid, salts of phenoisulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the active compounds and/or one of the inert carriers is insoluble in water and when the application takes place in water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc as further auxiliaries in the formulations and the use forms derived therefrom.

Stabilizers, such as low-temperature stabilizers, preservatives, antioxidants, light stabilizers or other agents which improve chemical and/or physical stability, may also be present. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Other possible auxiliaries are mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive customarily used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances Which are usually used for improving the penetration of agrochemical active compounds into plants. Penetrants are defined in this context by their ability to penetrate from the (generally aqueous) spray liquor and/or from the spray coating into the cuticle of the plant and thereby increase the mobility of active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The active compound content of the use forms prepared from the commercially available formulations may vary within wide limits. The active compound concentration of the use forms is in the range of from 0.00000001 to 97% by weight of active compound, preferably in the range of from 0.0000001 to 97% by weight, particularly preferably in the range of from 0.000001 to 83% by weight or 0.000001 to 97% by weight, and very particularly preferably in the range of from 0.0001 to 1% by weight.

The active compound combinations according to the invention can be present in their commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as fungicides and/or insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

When used as fungicides and/or insecticides, the active compound combinations according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example fruits, seeds, cuttings, tubers, rhizomes, slips, seed, bulbils, layers and runners.

Treatment according to the invention of the plants and plant parts with the active compound combinations is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats. Here, the active compound combinations can be prepared prior to the treatment by mixing the individual active compounds. Alternatively, the treatment is carried out successively by initially using a compound of the formula (I) or (I-1.), followed by treatment with an active compound of group II. However, it is also possible to treat the plants or plant parts first with an active compound of group II, followed by treatment with a compound of the formula I or (I-1).

The following plants may be mentioned as plants which can be treated according to the in invention: cotton, flax, grapevine, fruit, vegetables, such as *Rosaceae* sp. (for example pome fruits such as apples and pears, but also stone fruits such as apricots, cherries, almonds and peaches, and oft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as Wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pale choi, kohlrabi, radishes and oilseed rape, mustard, horseradish and cress), *Fabacae* sp. (for example beans, peanuts), *Papilionaceae* sp. (for example soya bean), *Solanaceae* sp. (for example potatoes), *Chenopodiaceae* sp. (for example sugar beet, fodder beet, Swiss chard, beetroot); useful plants and ornamental plants in gardens and forests.

Depending on the plant species or plant varieties, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processibility of the harvested products.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can further more be affected by improved plant architecture (under stress and non-stress conditions), including early flowering, flowering control for hybrid seed production, seedling vigour, plant size, internode number and distance, root growth, seed size, fruit size, pod size, pod or ear nuber, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, increased vigour, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant varieties (obtained by plant biotechnology methods) which may be treated according to the invention are herbicide-tolerant plants, i.e. plants made tolerant to one or more given herbicides. Such plants can be obtained by selection of plants containing a mutation imparting such herbicide tolerance.

The active compound combinations according to the invention are particularly suitable for the treatment of seed. Here, particular mention may be made of the combinations according to the invention mentioned above as preferred or particularly preferred. Thus, most of the damage to crop plants which is caused by phytopathogenic fungi and/or animal pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi and/or animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after sowing or after emergence of the plants. It is furthermore desirable to optimize the amount of active compound employed in such a way as to provide optimum protection for the seed and the germinating plant from attack by phytopathogenic fungi and/or animal pests, but without damaging the plant itself by the active compound employed. In particular, methods for the treatment of seed should also take into consideration the intrinsic fungicidal and/or insecticidal properties of transgenic plants in order to achieve optimum protection of the seed and the germinating plant with a minimum of crop protection products being employed.

Accordingly, the present invention also relates in particular to a method for protecting seed and germinating plants against attack by phytopathogenic fungi and/or animal pests by treating the seed with an active compound combination according to the invention. The method according to the invention for protecting seed and germinating plants against attack by phytopathogenic fungi and/or animal pests comprises a method where the seed is treated simultaneously with a compound of the formula (I) and an active compound from group (II) listed above. It also comprises a method where the seed is treated at different times with a compound of the formula (I) and an active compound from group (II) listed above.

The invention also relates to the use of the active compound combinations according to the invention for treating seed for protecting the seed and the germinating plant against phytopathogenic fungi and/or animal pests.

Furthermore, the invention relates to seed treated with an active compound comb nation according to the invention for protection against phytopathogenic fungi and/or animal pests. The invention also relates to seed which has been treated simultaneously with a compound of the formula (I) and an active compound from group II. The invention further relates to seed which has been treated at different times with a compound of the formula (I) and an active compound from group II. In the case of seed which has been treated at different times with a compound of the formula (I) and an active compound from group II, the individual active compounds of the inventive active compounds combination may be present in different layers on the seed. The layers comprising a compound of the formula (I) and an active compound from group II may optionally be separated by an intermediate layer. The invention also relates to seed wherein a compound of the formula (I) and an active compound from group II are applied as part of a coating or as a further layer or further layers in addition to a coating.

An advantage of the present invention is the synergistically increased insecticidal activity of the active compound combinations according to the invention in comparison with the individual insecticidally active compound, which exceeds the expected activity of the two active compounds when applied individually. Also advantageous is the synergictic enhancement of the fungicidal activity of the active compound combinations according to the invention compared with the individual fungicidally active compound, which exceeds the expected activity of the active compound applied individually. This makes possible an optimization of the amount of active compound employed.

It is likewise to be considered advantageous that the active compound combinations according to the invention can be used in particular also for transgenic seed.

The active compound combinations according to the invention are suitable for protecting seed of any plant variety as already mentioned above which is employed in agriculture, in the greenhouse, in forests or in horticulture. In particular, this takes the form of seed of maize, peanut, canola, oilseed, rape, poppy, soya beans, cotton, beet (for example sugar beet and fodder beet), rice, millet, wheat, barley, oats, rye, sunflower, tobacco, potatoes or vegetables (for example tomatoes, cabbage species, lettuce, etc.). The active compound combinations according to the invention are likewise suitable for treating the seed of fruit plants and vegetables as already mentioned above. The treatment of the seed of maize, soya beans, cotton, rice, beet, wheat and canola or oilseed rape is of particular importance.

Within the context of the present invention, the active compound combination according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the active compound combination according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples include the dyes known by the names Rhodamine B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be used in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz-und Schädlingsbekämpfringsmittel"

[Chemistry of the Crop Protection Compositions and Pesticides], Vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compound combinations according to the invention are also suitable for increasing the yield of crops. In addition, they have reduced toxicity and are well tolerated by plants.

The active compound combinations according to the invention also exhibit a potent strengthening effect in plants. They can therefore be used to mobilize the plant's own defences against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

In the present case, undesired microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The plants listed can be treated according to the invention in a particularly advantageous manner with the active compound mixtures according to the invention. The preferred ranges stated above for the active compound combinations also apply to the treatment of these plants. Particular emphasis is given to the treatment of plants with the active compound combinations specifically mentioned in the present text.

The good insecticidal and fungicidal action of the active compound combinations according to the invention can be seen from the examples which follow. While the individual active compounds show weaknesses in their action, the combinations show an action which exceeds a simple sum of actions.

A synergistic effect in insecticides and fungicides is always present when the insecticidal or fungicidal action of the active compound combinations exceeds the total of the actions of the active compounds when applied individually.

The expected insecticidal or fungicidal action for a given combination of two active compounds can be calculated according to S. R. Colby ("Calculating Synergistic and Antagonistic Responses of Herbicide Combinations", Weeds 1967, 15, 20-22), as follows:

If

X is the kill rate or efficacy, expressed in % of the untreated control, when the active compound A is used at an application rate of m ppm or g/ha, Y is the kill rate or efficacy, expressed in % of the untreated control, when the active compound B is used at an application rate of n ppm or g/ha, E is the kill rate or efficacy, expressed in % of the untreated control, when the active compounds A and B are used at respective application rates of m ppm and n ppm or g/ha, then $$E = X + Y - \frac{X \times Y}{100}.$$

Here, the kill rate or efficacy is determined in %. 0% means a kill rate or an efficacy that corresponds to that of the control, whereas a kill rate of 100% means that all animals are dead and an efficacy of 100% means that no infection is observed.

If the actual fungicidal or insecticidal activity exceeds the calculated value, the activity of the combination is super-additive, i.e. a synergistic effect is present. In this case, the actually observed efficacy must exceed the value calculated using the above formula for the expected efficacy (E).

EXAMPLE A

*Myzus persicae* Test

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by spraying with the active compound preparation of the desired concentration.

After the desired period of time, the kill in % is determined. 100% means that all of the aphids have been killed; 0% means that none of the aphids have been killed. The kill rates determined are entered into Colby's formula.

In this test, for example, the following active compound combinations in accordance with the present application show a synergistically enhanced activity compared to the active compounds applied individually:

TABLE A-1

*Myzus persicae* test

| Active compound | Concentration in g/ha | Kill in % after $1^d$ | |
| --- | --- | --- | --- |
| | | found* | calc.** |
| compound (I-1-1)/compound (I-1-7)*** | 4 | 0 | |
| metominostrobin | 100 | 0 | |
| compound (I-1-1)/compound (I-1-7)*** + metominostrobin (1:25) according to the invention | 4 + 100 | 70 | 0 |
| ipconazole | 100 | 0 | |
| compound (I-1-1)/compound (I-1-7)*** + ipconazole (1:25) according to the invention | 4 + 100 | 70 | 0 |
| mancozeb | 100 | 0 | |

TABLE A-1-continued

*Myzus persicae* test

| Active compound | Concentration in g/ha | Kill in % after $1^d$ | |
|---|---|---|---|
| | | found* | calc.** |
| compound (I-1-1)/compound (I-1-7)*** + mancozeb (1:25) according to the invention | 4 + 100 | 70 | 0 |
| mefenoxam | 100 | 0 | |
| | | found* | calc.** |
| compound (I-1-1)/compound (I-1-7)*** + mefenoxam (1:25) according to the invention | 4 + 100 | 70 | 0 |
| azoxystrobin | 100 | 0 | |
| | | found* | calc.** |
| compound (I-1-1)/compound (I-1-7)*** + azoxystrobin (1:25) according to the invention | 4 + 100 | 70 | 0 |

***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

TABLE A-2

*Myzus persicae* test

| Active compound | Concentration in g/ha | Kill in % after $5^d$ | |
|---|---|---|---|
| compound (I-1-2)/compound (I-1-8)*** | 0.16 | 0 | |
| tebuconazole | 100 | 0 | |
| | | found* | calc.** |
| compound (I-1-2)/compound (I-1-8)*** + tebuconazole (1:625) according to the invention | 0.16 + 100 | 70 | 0 |
| flutolanil | 100 | 0 | |
| | | found* | calc.** |
| compound (I-1-2)/compound (I-1-8)*** + flutolanil (1:625) according to the invention | 0.16 + 100 | 70 | 0 |

*found = activity found
**calc. = activity calculated using Colby's formula
***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

EXAMPLE B

*Phaedon cochleariae* Larvae Test

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emuisifier-containing water to the desired concentration.

Cabbage leaves (*Brassica oleracea*) are treated by spraying with the active compound preparation of the desired concentration and populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are entered into Colby's formula.

In this test, the following active compound combinations in accordance with the present application show a synergistically enhanced activity compared to the active compounds applied individually:

TABLE B-1

*Phaedon cochleariae* larvae test

| Active compound | Concentration in g/ha | Kill in % after $2^d$ | |
|---|---|---|---|
| compound (I-1-1)/compound (I-1-7)*** | 0.8 | 67 | |
| fluopyram | 100 | 0 | |
| | | found* | calc.** |
| compound (I-1-1)/compound (I-1-7)*** + fluopyram (1:125) according to the invention | 0.8 + 100 | 83 | 0 |

TABLE B-2

*Phaedon cochleariae* larvae test

| Active compound | Concentration in g/ha | Kill in % after $5^d$ | |
|---|---|---|---|
| compound (I-1-2)/compound (I-1-8)*** | 0.16 | 0 | |
| compound (I-1-1)/compound (I-1-7)*** | 0.16 | 0 | |
| prothioconazole | 100 | 0 | |
| | | found* | calc.** |
| compound (I-1-2)/compound (I-1-8)*** + prothioconazole (1:625) according to the invention | 0.16 + 100 | 100 | 0 |
| | | found* | calc.** |
| compound (I-1-1)/compound (I-1-7)*** + prothioconazole (1:625) according to the invention | 0.16 + 100 | 100 | 0 |
| tebuconazole | 100 | 0 | |
| | | found* | calc.** |
| compound (I-1-2)/compound (I-1-8)*** + tebuconazole (1:625) according to the invention | 0.16 + 100 | 100 | 0 |
| | | found* | calc.** |
| compound (I-1-1)/compound (I-1-7)*** + tebuconazole (1:625) according to the invention | 0.16 + 100 | 100 | 0 |
| triadimenol | 100 | 0 | |
| | | found* | calc.** |
| compound (I-1-2)/compound (I-1-8)*** + triadimenol (1:625) according to the invention | 0.16 + 100 | 33 | 0 |
| | | found* | calc.** |
| compound (I-1-1)/compound (I-1-7)*** + triadimenol (1:625) according to the invention | 0.16 + 100 | 100 | 0 |
| fluquinconazole | 100 | 0 | |
| | | found* | calc.** |
| compound (I-1-2)/compound (I-1-8)*** + fluquinconazole (1:625) according to the invention | 0.16 + 100 | 100 | 0 |

TABLE B-2-continued

*Phaedon cochleariae* larvae test

| Active compound | Concentration in g/ha | Kill in % after 5$^d$ | |
|---|---|---|---|
| | | found* | calc.** |
| compound (I-1-1)/compound (I-1-7)*** + fluquinconazole (1:625) according to the invention | 0.16 + 100 | 100 | 0 |
| fluoxastrobin | 100 | 0 | |
| | | found* | calc.** |
| compound (I-1-2)/compound (I-1-8)*** + fluoxastrobin (1:625) according to the invention | 0.16 + 100 | 33 | 0 |
| | | found* | calc.** |
| compound (I-1-1)/compound (I-1-7)*** + fluoxastrobin (1:625) according to the invention | 0.16 + 100 | 67 | 0 |
| trifloxystrobin | 100 | 0 | |
| | | found* | calc.** |
| compound (I-1-2)/compound (I-1-8)*** + trifloxystrobin (1:625) according to the invention | 0.16 + 100 | 67 | 0 |
| | | found* | calc.** |
| compound (I-1-1)/compound (I-1-7)*** + trifloxystrobin (1:625) according to the invention | 0.16 + 100 | 83 | 0 |
| triazoxide | 100 | 0 | |
| | | found* | calc.** |
| compound (I-1-2)/compound (I-1-8)*** + triazoxide (1:625) according to the invention | 0.16 + 100 | 67 | 0 |
| penflufen | 100 | 0 | |
| | | found* | calc.** |
| compound (I-1-1)/compound (I-1-7)*** + penflufen (1:625) according to the invention | 0.16 + 100 | 83 | 0 |
| fluopicolide | 100 | 0 | |
| | | found* | calc.** |
| compound (I-1-2)/compound (I-1-8)*** + fluopicolide (1:625) according to the invention | 0.16 + 100 | 33 | 0 |
| | | found* | calc.** |
| compound (I-1-1)/compound (I-1-7)*** + fluopicolide (1:625) according to the invention | 0.16 + 100 | 33 | 0 |
| fenamidone | 100 | 0 | |
| | | found* | calc.** |
| compound (I-1-2)/compound (I-1-8)*** + fenamidone (1:625) according to the invention | 0.16 + 100 | 100 | 0 |
| | | found* | calc.** |
| compound (I-1-1)/compound (I-1-7)*** + fenamidone (1:625) according to the invention | 0.16 + 100 | 100 | 0 |
| carpropamid | 100 | 0 | |
| | | found* | calc.** |
| compound (I-1-2)/compound (I-1-8)*** + carpropamid (1:625) according to the invention | 0.16 + 100 | 67 | 0 |
| | | found* | calc.** |
| compound (I-1-1)/compound (I-1-7)*** + carpropamid (1:625) according to the invention | 0.16 + 100 | 83 | 0 |
| isotianil | 100 | 0 | |

TABLE B-2-continued

*Phaedon cochleariae* larvae test

| Active compound | Concentration in g/ha | Kill in % after 5$^d$ | |
|---|---|---|---|
| | | found* | calc.** |
| compound (I-1-2)/compound (I-1-8)*** + isotianil (1:625) according to the invention | 0.16 + 100 | 100 | 0 |
| | | found* | calc.** |
| compound (I-1-1)/compound (I-1-7)*** + isotianil (1:625) according to the invention | 0.16 + 100 | 100 | 0 |
| pencycuron | 100 | 0 | |
| | | found* | calc.** |
| compound (I-1-1)/compound (I-1-7)*** + pencycuron (1:625) according to the invention | 0.16 + 100 | 100 | 0 |
| fludioxonil | 100 | 0 | |
| | | found* | calc.** |
| compound (I-1-2)/compound (I-1-8)*** + fludioxonil (1:625) according to the invention | 0.16 + 100 | 67 | 0 |
| ipconazole | 100 | 0 | |
| | | found* | calc.** |
| compound (I-1-2)/compound (I-1-8)*** + ipconazole (1:625) according to the invention | 0.16 + 100 | 33 | 0 |
| | | found* | calc.** |
| compound (I-1-1)/compound (I-1-7)*** + ipconazole (1:625) according to the invention | 0.16 + 100 | 100 | 0 |
| imazalil | 100 | 0 | |
| | | found* | calc.** |
| compound (I-1-2)/compound (I-1-8)*** + imazalil (1:625) according to the invention | 0.16 + 100 | 100 | 0 |
| mancozeb | 100 | 0 | |
| | | found* | calc.** |
| compound (I-1-1)/compound (I-1-7)*** + mancozeb (1:625) according to the invention | 0.16 + 100 | 83 | 0 |
| metalaxyl | 100 | 0 | |
| | | found* | calc.** |
| compound (I-1-1)/compound (I-1-7)*** + metalaxyl (1:625) according to the invention | 0.16 + 100 | 83 | 0 |
| mefenoxam | 100 | 0 | |
| | | found* | calc.** |
| compound (I-1-2)/compound (I-1-8)*** + mefenoxam (1:625) according to the invention | 0.16 + 100 | 83 | 0 |
| | | found* | calc.** |
| compound (I-1-1)/compound (I-1-7)*** + mefenoxam (1:625) according to the invention | 0.16 + 100 | 83 | 0 |
| sedaxane | 100 | 0 | |
| | | found* | calc.** |
| compound (I-1-1)/compound (I-1-7)*** + sedaxane (1:625) according to the invention | 0.16 + 100 | 100 | 0 |
| azoxystrobin | 100 | 0 | |
| | | found* | calc.** |
| compound (I-1-2)/compound (I-1-8)*** + azoxystrobin (1:625) according to the invention | 0.16 + 100 | 50 | 0 |

TABLE B-2-continued

Phaedon cochleariae larvae test

| Active compound | Concentration in g/ha | Kill in % after $5^d$ | |
|---|---|---|---|
| | | found* | calc.** |
| compound (I-1-1)/compound (I-1-7)*** + azoxystrobin (1:625) according to the invention | 0.16 + 100 | 83 | 0 |
| boscalid | 100 | 0 | |
| | | found* | calc.** |
| compound (I-1-1)/compound (I-1-7)*** + boscalid (1:625) according to the invention | 0.16 + 100 | 67 | 0 |
| flutolanil | 100 | 0 | |
| | | found* | calc.** |
| compound (I-1-1)/compound (I-1-7)*** + flutolanil (1:625) according to the invention | 0.16 + 100 | 83 | 0 |

*found = activity found
**calc. = activity calculated using Colby's formula
***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

EXAMPLE C

Spodoptera frugiperda Larvae Test

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration;

Cabbage leaves (Brassica oleracea) are treated by being sprayed with wits the preparation of active compound of the desired concentration and are populated with larvae of the armyworm (Spodoptera frugiperda) while the leaves are still moist.

After the desired period of time, the kill in % is deterirdned. 100% means that all caterpillars have been killed; 0% means that none of the caterpillars have been killed. The kill rates determined are entered into Colby's formula.

In this test, the following active compound combinations in accordance with the present application show a synergistically enhanced activity compared to the active compounds applied individually:

TABLE C-1

Spodoptera frugiperda larvae test

| Active compound | Concentration in g/ha | Kill in % after $2^d$ |
|---|---|---|
| compound (I-1-2)/compound (I-1-8)*** | 0.16 | 67 |
| compound (I-1-1)/compound (I-1-7)*** | 4 | 0 |
| | 0.8 | 0 |
| | 0.16 | 0 |
| penflufen | 100 | 0 |

TABLE C-1-continued

Spodoptera frugiperda larvae test

| Active compound | Concentration in g/ha | Kill in % after $2^d$ | |
|---|---|---|---|
| | | found* | calc.** |
| compound (I-1-2)/compound (I-1-8)*** + penflufen (1:625) according to the invention | 0.16 + 100 | 100 | 67 |
| imazalil | 100 | 0 | |
| | | found* | calc.** |
| compound (I-1-2)/compound (I-1-8)*** + imazalil (1:625) according to the invention | 0.16 + 100 | 100 | 67 |

*found = activity found
**calc. = activity calculated using Colby's formula
***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

TABLE C-2

Spodoptera frugiperda larvae test

| Active compound | Concentration in g/ha | Kill in % after $6^d$ | |
|---|---|---|---|
| compound (I-1-1)/compound (I-1-7)*** | 0.16 | 33 | |
| fosetyl-aluminium | 500 | 0 | |
| | | found* | calc.** |
| compound (I-1-1)/compound (I-1-7)*** + fosetyl-aluminium (1:3125) according to the invention | 0.16 + 500 | 67 | 33 |

*found = activity found
**calc. = activity calculated using Colby's formula
***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

EXAMPLE D

Aphis gossypii Test

| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Cotton plants (Gossypium hirsutum) severely infested by the cotton aphid (Aphis gossypii) are treated by spraying with the active compound preparation in the desired concentration.

After the desired period of time, the kill in % is determined. 100% means that all of the aphids have been killed; 0% means that none of the aphids have been killed. The kill rates determined a.re entered into Colby's formula.

In this test, the following active compound combination in accordance with the present application shows a synergistically enhanced activity compared to the compounds applied individually:

TABLE D

Aphis gossypii test

| Active compound | Concentration ppm | Kill in % after 1 d | |
|---|---|---|---|
| compound (I-1-1)/compound (I-1-7)*** | 4 | 10 | |
| 2,6-DIMETHYL-1H,5H-[1,4]DITHIINO[2,3-C:5,6-C']DIPYRROLE-1,3,5,7(2H,6H)-TETRONE | 500 | 0 | |
| | | found* | calc.** |
| compound (I-1-1)/compound (I-1-7)*** + 2,6-DIMETHYL-1H,5H-[1,4]DITHIINO[2,3-C:5,6-C']DIPYRROLE-1,3,5,7(2H,6H)-TETRONE (1:125) according to the invention | 4 + 500 | 45 | 10 |
| | | Kill in % after 2 d | |
| compound (I-1-1)/compound (I-1-7)*** | 20 | 35 | |
| fluopyram | 500 | 0 | |
| | | found* | calc.** |
| compound (I-1-1)/compound (I-1-7)*** + fluopyram (1:25) according to the invention | 20 + 500 | 60 | 35 |
| | | Kill in % after 3 d | |
| compound (I-1-2)/compound (I-1-8)*** | 4 | 10 | |
| 2,6-DIMETHYL-1H,5H-[1,4]DITHIINO[2,3-C:5,6-C']DIPYRROLE-1,3,5,7(2H,6H)-TETRONE | 500 | 0 | |
| | | found* | calc.** |
| compound (I-1-2)/compound (I-1-8)*** + 2,6-DIMETHYL-1H,5H-[1,4]DITHIINO[2,3-C:5,6-C']DIPYRROLE-1,3,5,7(2H,6H)-TETRONE (1:125) according to the invention | 4 + 500 | 65 | 10 |

*found = activity found
**calc. = activity calculated using the Colby formula
***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

EXAMPLE E

Myzus persicae Test (Run-Off Application)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amount of solvent and emulsifier, and the concentrate is diluted with emulsifier-containing water to the desired concentration.

Cabbage leaves (Brassica oleracea) which are heavily infested by the green peach aphid (Myzus persicae) are treated by spraying to run-off point with the active compound preparation of the desired concentration.

After the desired period of time, the kill in % is determined. 100% means that all of the aphids have been killed; 0% means that none of the aphids have been killed. The kill rates determined are entered into Colby's formula.

In this test, the following active compound combination in accordance with the present application shows a synergistically enhanced activity compared to the compounds applied individually:

TABLE E

Myzus persicae test

| Active compound | Concentration ppm | Kill in % after 1 d | |
|---|---|---|---|
| compound (I-1-1)/compound (I-1-7)*** | 4 | 50 | |
| 2,6-DIMETHYL-1H,5H-[1,4]DITHIINO[2,3-C:5,6-C']DIPYRROLE-1,3,5,7(2H,6H)-TETRONE | 500 | 0 | |
| | | found* | calc.** |
| compound (I-1-1)/compound (I-1-7)*** + 2,6-DIMETHYL-1H,5H-[1,4]DITHIINO[2,3-C:5,6-C']DIPYRROLE-1,3,5,7(2H,6H)-TETRONE (1:125) according to the invention | 4 + 500 | 70 | 50 |

*found = activity found
**calc. = activity calculated using the Colby formula
***In the mixtures tested of compound (I-1-1)/compound (I-1-7) or compound (I-1-2)/compound (I-1-8), the compounds (I-1-1) and (I-1-2) were in each case present in an amount of about 85% and about 84%, respectively, the compounds (I-1-7) and (I-1-8) were each present in an amount of about 15%.

The invention claimed is:

1. An active compound composition comprising a synergistically effective amount of a mixture of compounds of formula (I-1) selected from the group consisting of:

(I-1-1)

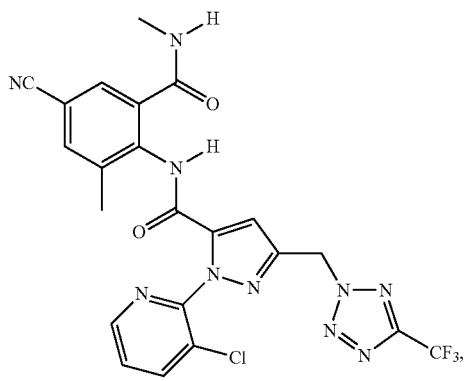

(I-1-7)

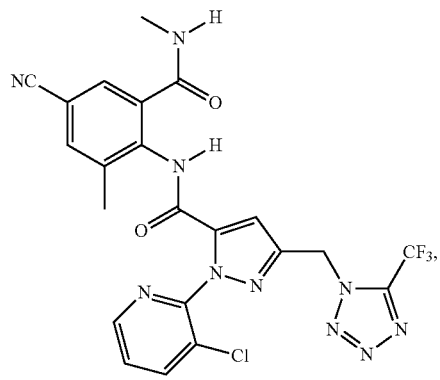

-continued

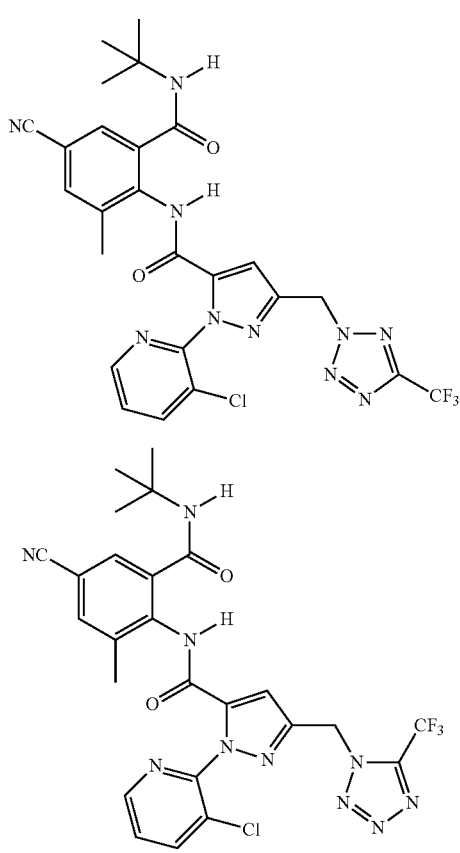

and bixafen.

2. An active compound composition according to claim 1 wherein a mixture of compounds of formula I-1-2 and I-1-8 is present.

3. An active compound composition according to claim 2, wherein the compounds of formulas I-1-2 and I-1-8 are present in a mixing ratio of 80:20 to 99:1.

4. An active compound composition according to claim 1, wherein the ratio of a compound of formula (I) or a mixture of compounds of the formula (I) to bixafen is from 625:1 to 1:625.

5. An active compound composition according to claim 1, wherein the ratio of a compound of formula (I) or a mixture of compounds of the formula (I) to bixafen is from 125:1 to 1:125.

6. An active compound composition according to claim 1, wherein the ratio of a compound of formula (I) or a mixture of compounds of the formula (I) to bixafen is from 25:1 to 1:25.

7. An active compound composition according to claim 1 wherein a mixture of compounds of formula I-1-1 and I-1-7 is present.

8. An active compound composition according to claim 7, wherein the ratio of a compound of the formula (I-1-1) to a compound of the Formula (I-1-7) is 80:20 to 99:1.

9. An agrochemical composition comprising an active compound composition according to claim 1, and also extenders and/or surfactants.

10. A seed treated with an active compound composition as defined in claim 1.

11. A method for controlling insect pests, comprising allowing the active compound composition as defined in claim 1, to act on insect pests and/or their habitat.

12. A method comprising treating seed with an active compound composition according to claim 9.

13. A method for controlling insect pests, comprising allowing the composition according to claim 9, to act on insect pests and/or their habitat.

14. A process for producing agrochemical compositions, wherein the active compound composition according to claim 1, are mixed with extenders and/or surfactants.

* * * * *